(12) United States Patent
Li et al.

(10) Patent No.: US 7,790,679 B2
(45) Date of Patent: Sep. 7, 2010

(54) PHARMACEUTICAL FORMULATIONS

(75) Inventors: Tiansheng Li, Newbury Park, CA (US); Christopher J. Sloey, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/499,607

(22) Filed: Aug. 4, 2006

(65) Prior Publication Data

US 2007/0053871 A1 Mar. 8, 2007

Related U.S. Application Data

(60) Provisional application No. 60/705,894, filed on Aug. 5, 2005.

(51) Int. Cl.
*A61K 38/18* (2006.01)

(52) U.S. Cl. .......................... 514/8; 530/399
(58) Field of Classification Search .................. None
See application file for complete search history.

(56) References Cited

U.S. PATENT DOCUMENTS

| | | | |
|---|---|---|---|
| 4,558,033 A | 12/1985 | Rudman | |
| 5,264,209 A | 11/1993 | Mikayama et al. | |
| 5,503,827 A | 4/1996 | Woog et al. | |
| 5,661,125 A | 8/1997 | Strickland | |
| 5,723,310 A * | 3/1998 | Builder et al. | 435/69.1 |
| 5,756,083 A | 5/1998 | Elliott | |
| 5,762,923 A | 6/1998 | Gross et al. | |
| 5,795,569 A | 8/1998 | Bartley et al. | |
| 5,856,298 A | 1/1999 | Strickland | |
| 5,919,911 A | 7/1999 | Broudy et al. | |
| 5,989,538 A | 11/1999 | Elliott | |
| 6,171,586 B1 | 1/2001 | Lam et al. | |
| 6,207,802 B1 | 3/2001 | Zsebo et al. | |
| 6,267,958 B1 | 7/2001 | Andya et al. | |
| 6,303,113 B1 | 10/2001 | Woog et al. | |
| 6,458,924 B2 | 10/2002 | Knudsen et al. | |
| 6,531,448 B1 | 3/2003 | Brader | |
| 6,696,056 B1 | 2/2004 | Cheung et al. | |
| 6,821,515 B1 | 11/2004 | Cleland et al. | |
| 6,835,536 B2 | 12/2004 | Krieger et al. | |
| 6,896,885 B2 | 5/2005 | Hanna | |
| 6,908,935 B2 | 6/2005 | Kelly et al. | |
| 6,964,967 B2 | 11/2005 | Huang et al. | |
| 6,967,254 B2 | 11/2005 | Dominguez et al. | |
| 7,053,088 B2 | 5/2006 | Doherty et al. | |
| 7,053,215 B2 | 5/2006 | Medina et al. | |
| 7,169,754 B2 * | 1/2007 | Papadimitriou | 514/8 |
| 2001/0031726 A1 | 10/2001 | Van Antwerp et al. | |
| 2005/0080011 A1 | 4/2005 | Somers et al. | |
| 2005/0267027 A1 * | 12/2005 | Lounsbury et al. | 514/12 |

FOREIGN PATENT DOCUMENTS

| | | |
|---|---|---|
| EP | 0 280 358 | 8/1988 |
| WO | WO 00/24782 | 5/2000 |
| WO | WO 00/61169 | 10/2000 |
| WO | WO 03/020299 | 3/2003 |

OTHER PUBLICATIONS

Athawale et al. Osmolyte Trimethylamine-N-oxide Does Not Affect the Strength of Hydrophobic Interactions:Origin of of Osmolyte Compatibility. Biophysical Journal 89:858-866 (May 13, 2005).*
Thirumangalathu et al., "Effects of pH, Temperature, and Sucrose on Benzyl Alcohol-Induced Aggregation of Recombinant Human Granulocyte Colony Stimulating Factor", Journal of Pharmaceutical Sciences, 95(7):1480-1497 (2006).
Cadot et al., "The effect of sucrose on the quality of ryegrass (*Lolium perenne*) pollen extracts", *Allergy*, 50:941-951 (1995).
Chu et al., "A comprehensive picture of non-site specific oxidation of methionine residues by peroxides in protein pharmaceuticals", *J. Pharm. Sci.*, 93(12):3096-3102 (2004).
Cotes and Bangham, Bio-assay of erythropoietin in mice made polycythaemic by exposure to air at a reduced pressure, *Nature*, 191:1065 (1961).
Rodrigues-Silva et al., "Thermal stability studies of hyperimmune horse antivenoms", Toxicon., 37(1):33-45 (1999).
Egrie et al., Development and characterization of novel erythropoiesis stimulating protein (NESP). *British Journal of Cancer*. 84 (Suppl. 1): 3-10 (2001).

* cited by examiner

*Primary Examiner*—Marianne P Allen
*Assistant Examiner*—Regina M DeBerry
(74) *Attorney, Agent, or Firm*—Michael G. Penn

(57) ABSTRACT

A method of stabilizing an aqueous protein or antibody formulation is disclosed herein. Additionally, stable pharmaceutical formulations are contemplated which comprise a biologically active protein, a destabilizing concentration of preservative and a stabilizing concentration of osmolyte.

29 Claims, 18 Drawing Sheets

Anti-Streptavidin – Near UV CD – 295nm

Anti-Streptavidin – Near UV CD – 295nm

Anti-Streptavidin – Near UV CD – 295nm

Anti-Streptavidin – Near UV CD – 295nm

Herceptin – Near UV CD – 295nm

Rituxan – Near UV CD – 295nm

864G1 – 5 days 52C – SEC-HPLC

864G1 – Near UV CD – 295nm

864G1 – Near UV CD – 295nm

864G1 – Near UV CD – 295nm

864G1 – Near UV CD – 295nm

864G1 – 4 days 45C – SEC-HPLC

864G1 – 4 days 52C – SEC-HPLC

PHARMACEUTICAL FORMULATIONS

FIELD OF THE INVENTION

The present invention relates to stable aqueous pharmaceutical formulations of proteins. In particular, the present invention relates to aqueous pharmaceutical formulations of proteins with destabilizing amounts of preservatives and stabilizing amounts of osmolytes that counteract the destabilization caused by the preservative.

BACKGROUND OF THE INVENTION

Pharmaceutically active proteins are frequently formulated in aqueous solutions, particularly for parenteral injection. The pharmaceutical composition may be sold commercially in a ready-to-use solution form or may be provided in a lyophilized form that is reconstituted with an aqueous solution. For products that need to be administered in multiple doses, it is beneficial to be able to withdraw several doses from a single vial, i.e., providing the product as a multi-dose product rather than a single-dose product. Multi-dose products usually must include an antimicrobial preservative that kills or inhibits the growth of any microbes which may inadvertently be introduced into the container. The presence of the preservative thus prevents microbial growth and subsequent administration of such microbes to the patient.

However, many preservatives, especially those containing aromatic functional groups, have been found to destabilize the tertiary structure of active proteins. The consequent denaturation, or a breakdown of a protein's tertiary structure, can result in unfolded or improperly folded inactive protein. This frequently manifests as degradation, precipitation and/or aggregation of the protein, effects that are commercially undesirable. At its most extreme, the degraded or aggregated protein can cause an immunogenic response.

Thus, there remains a need for improved formulations of proteins that contain preservatives. In particular, there is a need for an aqueous pharmaceutical formulation that exhibits improved stability in the presence of a destabilizing preservative.

SUMMARY OF THE INVENTION

The present invention is directed toward methods of stabilizing a pharmaceutical formulation by combining an osmolyte, preservative, and therapeutic or pharmaceutically active protein in an aqueous solution. The present invention is further directed toward stable pharmaceutical formulations produced by this process, wherein the formulations contain biologically active polypeptides, destabilizing concentrations of preservatives and stabilizing concentrations of osmolytes. A variety of pharmaceutically active proteins are contemplated for use in the formulations of the invention, including antibodies and other non-antibody proteins. Exemplary antibodies include antibodies that bind to Her2 or CD20. Exemplary proteins include human erythropoietin (SEQ. ID NO.: 2) or biologically active variants, derivatives, or analogs thereof, including chemically modified derivatives of such proteins or analogs. Amino acids 28 through 192 of SEQ. ID NO: 2 constitute the mature protein. One preferred polypeptide is Darbepoetin (SEQ. ID NO: 1). Amino acids 1 through 164 of SEQ. ID NO: 1 constitutes the mature protein. Also preferred are analogs of erythropoietin (SEQ. ID NO.: 2) or Darbepoetin (SEQ. ID NO: 1), with 65%, 70%, 75%, 80%, 85%, 90%, 91%, 92%, 93%, 94%, 95%, 96%, 97%, 98%, or 99% homology to SEQ. ID NO: 2 or SEQ. ID NO: 1, respectively, and still retaining activity to stimulate erythropoiesis as demonstrated in an in vivo assay, for example, the exhypoxic polycythermic mouse assay. See, e.g., Cotes and Bangham, *Nature,* 191:1065 (1961).

Thus, in one embodiment the invention provides stable pharmaceutical formulations containing a biologically active protein, a destabilizing concentration of a preservative and a concentration of osmolyte from about 0.35 to about 6M that provides a stabilizing effect on the protein. Also contemplated is a concentration of osmolyte of about 0.20 to about 6M. Preferably the stabilizing effect results in a shelf life at 2-8° C. (refrigerator temperature) of at least two months, or at least 3, 6, 9, 12, 18 or 24 months. According to the invention, a single osmolyte or a combination of multiple osmolytes may be used. In some embodiments, the concentration of destabilizing preservative present in the formulation is from about 0.001 M to about 0.15 M. Preferably the formulation contains a preservative, or combination of preservatives, that exhibits the least destabilizing effect. Preferred destabilizing preservatives include benzyl alcohol and benzalkonium chloride. Exemplary osmolytes include glycerol, sorbitol, sarcosine, glycine, proline, sucrose, betaine, taurine, or trimethylamine N-oxide (TMAO), or mixtures thereof.

In specific embodiments, the invention provides a stable pharmaceutical formulation of Darbepoetin (SEQ. ID NO: 1), a destabilizing concentration of preservative, and a concentration of osmolyte from about 0.35 to about 6M that provides a stabilizing effect on the protein. Also contemplated is a concentration of osmolyte of about 0.20 to about 6 M. Preferred preservatives include benzyl alcohol and benzalkonium chloride. Preferred osmolytes include glycerol, glycine, betaine, taurine, proline or TMAO, or mixtures thereof. In some embodiments, the osmolyte is a low molecular weight organic compound, wherein its molecular weight is less than 1000 but greater than 76 Da. In certain embodiments, the osmolyte is less than 750 Da, less than 500 Da, or less than 300 Da.

In other specific embodiments, the invention provides a stable pharmaceutical formulation of an antibody, a destabilizing concentration of preservative, and a concentration of osmolyte from about 0.35 to about 6M that provides a stabilizing effect on the antibody. Also contemplated is a concentration of osmolyte of about 0.20 to about 6 M. Exemplary antibodies include antibodies that bind to CD20 or Her2. Preferred preservatives include benzyl alcohol and benzalkonium chloride. Preferred osmolytes include glycerol, glycine, sarcosine, betaine, taurine, sucrose, or sorbitol or mixtures thereof. Also preferred in antibody formulations is the osmolyte trimethylamine N-oxide, when the pH of formulation is greater than 6.0.

One embodiment of the present invention provides stable aqueous pharmaceutical formulations of Darbepoetin (SEQ. ID NO: 1) that include benzalkonium chloride and glycerol. Exemplary formulations include protein at a concentration ranging from about 0.1 mg/mL to about 180 mg/mL, about 0.3 mg/mL to about 150 mg/mL, or about 0.5 mg/mL to about 3 mg/mL; benzalkonium chloride at a concentration of up to about 0.02 M, or ranging from about 0.005 to about 0.02 M, or ranging from about 0.005 to about 0.1M, and glycerol at a concentration ranging from about 2.5 to about 6 M, or about 5 to about 5.7 M. In one embodiment, the formulation includes Darbepoetin (SEQ. ID NO: 1) at a concentration ranging from about 0.5 to about 3 mg/mL, benzalkonium chloride at a concentration ranging from about 0.005 to about 0.01 M, and glycerol at a concentration ranging from about 5 to about 5.7 M.

Another embodiment of the present invention provides stable aqueous pharmaceutical formulations of Darbepoetin (SEQ. ID NO.: 1) that include benzyl alcohol and glycerol. Exemplary formulations include protein at a concentration ranging from about 0.1 mg/mL to about 180 mg/mL, about 0.3 mg/mL to about 150 mg/mL, or about 0.5 mg/mL to about 3 mg/mL; benzyl alcohol at a concentration of up to about 0.15 M, or ranging from about 0.075 to about 0.15 M, or about 0.13 to about 0.15M; and glycerol at a concentration ranging from about 2.5 to about 6 M, or about 5 to about 5.7 M. In one embodiment, the formulation includes Darbepoetin (SEQ. ID NO: 1) at a concentration ranging from about 0.5 to about 3 mg/mL, benzyl alcohol at a concentration ranging from about 0.13 to about 0.15 M, and glycerol at a concentration ranging from about 5 to about 5.7 M.

Another embodiment of the present invention provides stable aqueous pharmaceutical formulations of Darbepoetin (SEQ. ID NO.: 1) that include benzyl alcohol and trimethylamine N-oxide (TMAO). Exemplary formulations include protein at a concentration ranging from about 0.1 mg/mL to about 180 mg/mL, about 0.3 mg/mL to about 150 mg/mL, or about 0.5 to about 3 mg/mL; benzyl alcohol at a concentration of up to about 0.15 M, or ranging from about 0.075 to about 0.15 M, or about 0.13 to about 0.15 M; and TMAO at a concentration ranging from about 0.85 to about 1.15 M, or about 0.5 to about 1.5 M. In one embodiment, the formulation includes Darbepoetin (SEQ. ID NO: 1) at a concentration ranging from about 0.5 to about 3 mg/mL, benzyl alcohol at a concentration ranging from about 0.13 to about 0.15 M, and trimethylamine N-oxide at a concentration ranging from about 0.85 to about 1.15 M.

Yet another embodiment of the present invention provides stable aqueous pharmaceutical formulations of Darbepoetin (SEQ. ID NO.: 1) that include benzyl alcohol and proline. Exemplary formulations include the protein at a concentration ranging from about 0.1 mg/mL to about 180 mg/mL, about 0.3 mg/mL to about 150 mg/mL, or about 0.5 to about 3 mg/mL; benzyl alcohol at a concentration of up to about 0.15 M, or ranging from about 0.075 to about 0.15 M, or about 0.13 to about 0.15 M; and proline at a concentration ranging from about 0.5 to about 1.5 M, or about 0.85 to about 1.15 M. In one embodiment, the formulation includes Darbepoetin (SEQ. ID NO: 1) at a concentration ranging from about 0.5 to about 3 mg/mL, benzyl alcohol at a concentration ranging from about 0.13 to about 0.15 M, and proline at a concentration ranging from about 0.85 to about 1.15 M.

Another embodiment of the present invention provides stable aqueous pharmaceutical formulations of granulocyte-colony stimulating factor (GCSF) that include benzyl alcohol and an osmolyte. Exemplary formulations include the protein at a concentration ranging from about 0.1 mg/mL to about 180 mg/mL, about 0.3 mg/mL to about 150 mg/mL, or about 0.5 to about 3 mg/mL; and benzyl alcohol at a concentration ranging from about 0.05 to about 0.5 M, preferably about 0.05 to about 0.125 M. In one embodiment, the formulation includes GCSF at a concentration ranging from about 0.05 to about 20 mg/mL, benzyl alcohol at a concentration ranging from about 0.05 to about 0.125 M, and an osmolyte present at a concentration of about 0.3 to about 1.5 M. Exemplary osmolytes include sorbitol, glycerol, and sarcosine.

Still another embodiment of the present invention provides stable aqueous pharmaceutical formulations of an antibody that include benzyl alcohol and glycerol. Exemplary formulations include the antibody at a concentration ranging from about 0.1 to about 180 mg/mL, about 0.3 mg/mL to about 150 mg/mL, or about 0.5 to about 3 mg/mL; benzyl alcohol at up to 0.15 M, or ranging from about 0.075 to about 0.15 M, or about 0.075 to about 0.105 M; and glycerol at a concentration ranging from about 2.5 to about 6 M, or about 5 to about 5.7 M. In one embodiment, the formulation includes an antibody at a concentration ranging from about 0.5 to about 3 mg/mL, benzyl alcohol at a concentration ranging from about 0.075 to about 0.105 M, and glycerol at a concentration ranging from about 5 to about 5.7 M.

Yet another embodiment of the present invention provides stable aqueous pharmaceutical formulations of an antibody that include benzyl alcohol, glycerol and glycine. Exemplary formulations include the antibody at a concentration ranging from about 0.1 to about 180 mg/mL, about 0.3 mg/mL to about 150 mg/mL, or about 0.5 to about 3 mg/mL; benzyl alcohol at up to 0.15 M, or ranging from about 0.075 to about 0.15 M, or about 0.075 to about 0.105 M; glycerol at a concentration ranging from about 0.75 to about 2 M, or about 0.85 to about 1.5 M; and glycine at a concentration ranging from about 0.75 to about 1.5M, or about 0.85 to about 1.15 M. In one embodiment, the formulation includes an antibody at a concentration ranging from about 0.5 to about 3 mg/mL, benzyl alcohol at a concentration ranging from about 0.075 to about 0.105 M, glycerol at a concentration ranging from about 1 to about 1.5 M and glycine at a concentration ranging from about 0.85 to about 1.15 M.

Still another embodiment of the present invention provides stable aqueous pharmaceutical formulations of an antibody that include benzyl alcohol, and sarcosine. Exemplary formulations include the antibody at a concentration ranging from about 0.1 to about 180 mg/mL, about 0.3 mg/mL to about 150 mg/mL, or about 0.5 to about 3 mg/mL; benzyl alcohol at up to 0.15 M, or ranging from about 0.075 to about 0.15 M, or about 0.075 to about 0.105 M; and sarcosine at a concentration ranging from about 0.5 to about 1.15 M, or about 0.85 to about 1.15 M. In one embodiment, the formulation includes an provides stable aqueous pharmaceutical formulations comprising an antibody at a concentration ranging from about 0.5 to about 3 mg/mL, benzyl alcohol at a concentration ranging from about 0.075 to about 0.105 M, glycerol at a concentration ranging from about 1 to about 1.5 M and glycine at a concentration ranging from about 0.85 to about 1.15 M.

Yet another embodiment of the present invention provides stable aqueous pharmaceutical formulations of an antibody that include benzyl alcohol and sucrose. Exemplary formulations include the antibody at a concentration ranging from about 0.1 to about 180 mg/mL, about 0.3 mg/mL to about 150 mg/mL, or about 0.5 to about 3 mg/mL; benzyl alcohol at up to 0.15 M, or ranging from about 0.075 to about 0.15 M, or about 0.075 to about 0.105 M; and sucrose at a concentration ranging from about 0.5 to about 1.15 M, or about 0.85 to about 1.15 M. In one embodiment, the formulation includes an provides stable aqueous pharmaceutical formulations comprising an antibody at a concentration ranging from about 0.5 to about 3 mg/mL, benzyl alcohol at a concentration ranging from about 0.075 to about 0.105 M, and sucrose at a concentration ranging from about 0.85 to about 1.15 M.

Still another embodiment of the present invention provides stable aqueous pharmaceutical formulations of an antibody that include benzyl alcohol and sorbitol. Exemplary formulations include the antibody at a concentration ranging from about 0.1 to about 180 mg/mL, about 0.3 mg/mL to about 150 mg/mL, or about 0.5 to about 3 mg/mL; benzyl alcohol at up to 0.15 M, or ranging from about 0.075 to about 0.15 M, or about 0.075 to about 0.105 M; and sorbitol at a concentration ranging from about 0.5 to about 2.5 M, or about 2.1 to about 2.3 M. In one embodiment, the formulation includes an provides stable about 0.5 to about 3 mg/mL, benzyl alcohol at a concentration ranging from about 0.075 to aqueous pharmaceutical formulations comprising an antibody at a concentration ranging from about 0.105 M, and sorbitol at a concentration ranging from about 2.1 to about 2.3 M.

Yet another embodiment of the present invention provides stable aqueous pharmaceutical formulations of an antibody that include benzyl alcohol and betaine. Exemplary formulations include the antibody at a concentration ranging from about 0.1 to about 180 mg/mL, about 0.3 mg/mL to about 150 mg/mL, or about 0.5 to about 3 mg/mL; benzyl alcohol at up to 0.15 M, or ranging from about 0.075 to about 0.15 M, or about 0.075 to about 0.105 M; and betaine at a concentration ranging from about 0.07 to about 2.5 M, or about 0.1 to about 1.25 M. In one embodiment, the formulation includes an antibody at a concentration ranging from about 0.5 to about 3 mg/mL, benzyl alcohol at a concentration ranging from about 0.075 to about 0.105 M, and betaine at a concentration ranging from about 0.2 to about 1.0 M.

Still another embodiment of the present invention provides stable aqueous pharmaceutical formulations of an antibody that include benzyl alcohol and taurine. Exemplary formulations include the antibody at a concentration ranging from about 0.1 to about 180 mg/mL, about 0.3 mg/mL to about 150 mg/mL, or about 0.5 to about 3 mg/mL; benzyl alcohol at up to 0.15 M, or ranging from about 0.075 to about 0.15 M, or about 0.075 to about 0.105 M; and taurine at a concentration ranging from about 0.07 to about 2.5 M, or about 0.1 to about 1.25 M. In one embodiment, the formulation includes an antibody at a concentration ranging from about 0.5 to about 3 mg/mL, benzyl alcohol at a concentration ranging from about 0.075 to about 0.105 M, and taurine at a concentration ranging from about 0.2 to about 1.0 M.

Another embodiment of the present invention provides stable aqueous pharmaceutical formulations of an antibody that include m-cresol and glycerol. Exemplary formulations include the antibody at a concentration ranging from about 0.1 to about 180 mg/mL, about 0.3 mg/mL to about 150 mg/mL, or about 0.5 to about 5 mg/mL; m-cresol at up to 0.01 M, or ranging from about 0.0005 to about 0.005 M, or from about 0.0005 to about 0.002 M; and glycerol at a concentration ranging from about 2.5 to about 6 M, or about 5 to about 5.7 M. In one embodiment, the formulation includes an antibody at a concentration ranging from about 0.5 to about 5 mg/mL, m-cresol at a concentration ranging from about 0.0005 to about 0.002 M, and glycerol at a concentration ranging from about 5 to about 5.7 M.

Another embodiment of the present invention provides methods of preparing a lyophilized powder from any of the disclosed stable aqueous formulations. The lyophilized powder is prepared via lyophilizing a stable aqueous protein or antibody formulation as described herein. Also provided are methods of reconstituting a lyophilized powder by adding a sterile aqueous diluent to the powder.

Further embodiments of the present invention provide methods of screening for optimal stabilizing concentrations of an osmolyte by comparing the stability of two or more formulations having different osmolyte concentrations. In some embodiments, the stability is measured by circular dichroism or size exclusion chromatography.

DETAILED DESCRIPTION OF THE INVENTION

Figure 1:
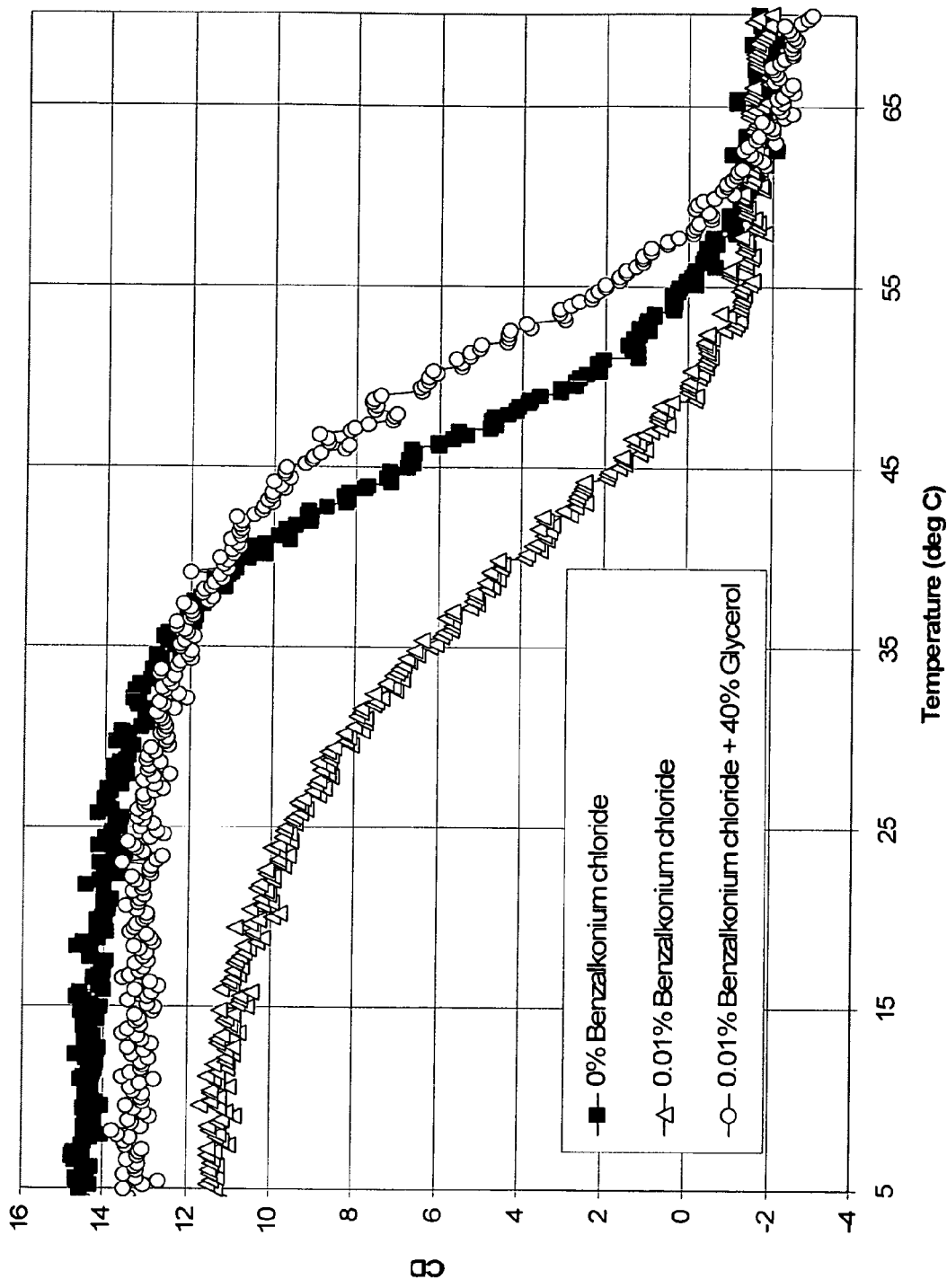
FIG. 1 is a representative graph displaying the effect of the destabilizing preservative benzalkonium chloride on the stability of Darbepoetin in the presence and absence of the osmolyte glycerol, as measured using circular dichroism (CD).

Preservatives promote unfolding of the tertiary structure of a protein of interest when used in amounts sufficient to prevent or retard microbial growth. Selected osmolytes at selected concentrations have been discovered to mitigate the destabilizing effect of preservatives on proteins. Thus, the invention contemplates a method for stabilizing aqueous protein formulations by combining an osmolyte, a preservative, and a therapeutic protein in an aqueous solution, where the concentration of the preservative would otherwise destabilize the protein yet the concentration of osmolyte mitigates the destabilizing effect of the preservative.

As shown herein, the addition of one or more osmolytes to a formulation that contains a biologically active protein and a destabilizing preservative results in a formulation that is more stable than the formulation without the osmolyte(s) and that has an increased shelf life, particularly at refrigerator temperature. Also provided herein are methods for screening one or more formulations, each containing different concentrations of osmolytes, and comparing stability of the formulations to identify the osmolyte concentration that provides a more stable formulation or increased shelf life. Further provided are methods of preparing a lyophilized powder from the stable aqueous formulations disclosed herein and methods of reconstituting the disclosed lyophilized powders via addition of a sterile aqueous diluent. Generally the concentration of osmolyte is much greater than that of the preservative. This higher concentration of osmolyte allows for the mitigation of the destabilizing effects of the destabilizing preservative.

Thus, the present invention provides stable pharmaceutical formulations containing biologically active polypeptides, destabilizing concentrations of preservatives and stabilizing concentrations of osmolytes. Any of the polypeptides described herein may be combined with any of the preservatives described herein and any of the osmolytes described herein, with each component present at any of the respective concentrations or ranges described herein.

Formulations of the invention preferably also include pharmaceutically acceptable buffers, such as acetate (e.g. sodium acetate), succinate (such as sodium succinate), gluconate, histidine, citrate or other organic acid buffers. Exemplary buffer concentration can be from about 1 mM to about 200 mM, or from about 10 mM to about 60 mM, depending, for example, on the buffer and the desired isotonicity of the formulation. Exemplary pHs include from about 4.5 to about 6.5, or from about 4.8 to about 5.5, or alternatively about 5. Also contemplated are protein formulations having a pH above about 6.5, or above about 7.0. In such formulations, osmolytes such as trimethylamine N-oxide (TMAO), which have a ionizable group (pK$_a$ about 4.5) and may not perform optimally at lower pHs, are typically preferred. However, any osmolyte can be added to such formulations to stabilize the protein in the presence of the destabilizing amount of a preservative. Also contemplated are diluents as described in U.S. Pat. Nos. 7,053,215; 7,053,088; 6,967,254; 6,964,967; 6,908, 935; 6,207,802; 5,989,538; 5,856,298; 5,795,569; 5,756,083; 5,264,209; and 4,558,033, each of which is incorporated in its entirety by reference herein.

Formulations of the invention may optionally include pharmaceutically acceptable salts, such as sodium chloride, and may optionally include surfactants, but generally osmolyte alone (without surfactant) is sufficient to stabilize the biologically active protein. The formulations may additionally or alternatively include a diluent, excipient, or carrier, and/or other formulation agents. Suitable diluents, excipients, or carriers and other agents include, but are not limited to, antioxidants, coloring, flavoring and diluting agents, emulsifying agents, suspending agents, solvents, fillers, bulking agents, buffers, vehicles, diluents, excipients and/or pharmaceutical adjuvants. For example, a suitable vehicle may be, physiological saline solution, citrate buffered saline, or artificial CSF, possibly supplemented with other materials common in compositions for parenteral administration. Neutral buffered saline or saline mixed with serum albumin are further exemplary vehicles. Those skilled in the art would readily recognize a variety of buffers that could be used in the compositions, and dosage forms used in the invention. Typical buffers include, but are not limited to pharmaceutically acceptable weak acids, weak bases, or mixtures thereof. Preferably, the buffer components are water soluble materials such as phosphoric acid, tartaric acids, lactic acid, succinic acid, citric acid, acetic acid, ascorbic acid, aspartic acid, glutamic acid, and salts thereof.

As used herein, a "destabilizing" effect is an increase in the tendency of a protein to unfold. Thus, a "destabilizing" concentration of preservative causes an increase in unfolding, or in other words, a decrease in stability.

Stability can be assessed in many ways, including monitoring conformational change over a range of temperatures (thermostability) and/or time periods (shelf-life) and/or after exposure to stressful handling situations (e.g. physical shaking). Stability of formulations containing varying concentrations of formulation components can be measured using a variety of methods. For example, the amount of protein aggregation can be measured by visual observation of turbidity, by measuring absorbance at a specific wavelength, by size exclusion chromatography (in which aggregates of a protein will elute in different fractions compared to the protein in its native active state), HPLC, or other chromatographic methods. Other methods of measuring conformational change can be used, including using differential scanning calorimetry (DSC), e.g. to determine the temperature of denaturation, or circular dichroism (CD), which measures the molar ellipticity of the protein. Fluorescence can also be used to analyze the composition. Fluorescence encompasses the release or absorption of energy in the form of light or heat, and changes in the polar properties of light. Fluorescence emission can be intrinsic to a protein or can be due to a fluorescence reporter molecule. For example, ANS is a fluorescent probe that binds to the hydrophobic pockets of partially unfolded proteins. As the concentration of unfolded protein increases, the number of hydrophobic pockets increases and subsequently the concentration of ANS that can bind increases. This increase in ANS binding can be monitored by detection of the fluorescence signal of a protein sample. Other means for measuring stability can be used and are well known to persons of skill in the art.

As used herein, "stable" formulations of biologically active proteins are formulations that exhibit less denaturation or loss of biological activity compared with a control sample. Any of the methods described immediately above can be used to measure stability.

As used herein, "pharmaceutical formulation" is a composition of a pharmaceutically active drug, such as a biologically active protein, that is suitable for parenteral administration (including but not limited to intravenous, intramuscular, or subcutaneous) to a patient in need thereof and includes only pharmaceutically acceptable excipients, diluents, and other additives deemed safe by the Federal Drug Administration or other foreign national authorities. Specifically excluded from the scope of the term "pharmaceutical formulation" are compositions for ophthalmic or topical administration to patients.

The formulations disclosed herein are particularly well-suited for multidose formulations as they contain a preservative. Therefore, in various embodiments, the therapeutic protein and/or antibody are prepared in multidose formulations. A multidose formulation is a formulation having more than one dose of the therapeutic protein or antibody. The healthcare provider and/or patient can administer a single dose from the multidose formulation, storing the remainder of the formulation for future administration in one or more subsequent doses. The number of doses in the multidose formulations disclosed herein can be about 2 to about 50, preferably about 2 to about 40, and more preferably about 2 to about 25. Also contemplated are doses of at least 5, at least 10, and at least 20. Specific doses include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 doses in the formulation.

The terms "polypeptide" and "protein" are used interchangeably herein.

Exemplary polypeptides contemplated for use in the stable pharmaceutical formulations of the invention include antibodies, peptibodies, immunoglobulin-like proteins, non-antibody proteins and non-immunoglobulin-like proteins. Analogs of naturally occurring proteins are contemplated for inclusion in formulations of the present invention, including polypeptides with modified glycosylation, polypeptides without glycosylation (unglycosylated). As used herein, "analogs" refers to an amino acid sequence that has insertions, deletions or substitutions relative to the parent sequence, while still substantially maintaining the biological activity of the parent sequence, as determined using biological assays known to one of skill in the art. The formulations of the invention may also include derivatives of naturally occurring or analog polypeptides which have been chemically modified, for example, to attach water soluble polymers (e.g., pegylated), radionuclides, or other diagnostic or targeting or therapeutic moieties.

Exemplary polypeptides include human erythropoietin or biologically active variants, derivatives, or analogs thereof, including chemically modified derivatives. One preferred protein is Darbepoetin (SEQ. ID NO: 1). Darbepoetin is a hyperglycosylated erythropoietin analog having five changes in the amino acid sequence of rHuEPO which provide for two additional carbohydrate chains. More specifically, Darbepoetin contains two additional N-linked carbohydrate chains at amino acid residues 30 and 88 of SEQ. ID. NO: 2.

Other examples of proteins include granulocyte-colony stimulating factor (GCSF), stem cell factor, leptin, hormones, cytokines, hematopoietic factors, growth factors, antiobesity factors, trophic factors, anti-inflammatory factors, receptors or soluble receptors, enzymes, variants, derivatives, or analogs of any of these proteins. Other examples include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase, or kallikrein, receptors or soluble receptors, enzymes, variants, derivatives, or analogs of any of these proteins.

Antibodies may be formulated according to the present invention. As used herein, the term "antibody" includes fully assembled antibodies, monoclonal antibodies (including human, humanized or chimeric antibodies), polyclonal antibodies, multispecific antibodies (e.g., bispecific antibodies), Maxibody, and antibody fragments that can bind antigen (e.g., Fab', F'(ab)2, Fv, single chain antibodies, diabodies), comprising complementarity determining regions (CDRs) of the foregoing as long as they exhibit the desired biological activity.

Exemplary antibodies are Herceptin® (Trastuzumab), a recombinant DNA-derived humanized monoclonal antibody that selectively binds to the extracellular domain of the human epidermal growth factor receptor 2 (Her2) proto-oncogene; and Rituxan® (Rituximab), a genetically engineered chimeric murine/human monoclonal antibody directed against the CD20 antigen found on the surface of normal and malignant B lymphocytes. Other exemplary antibodies include Avastin® (bevacizumab), Bexxar® (Tositumomab), Campath® (Alemtuzumab), Erbitux® (Cetuximab), Humira® (Adalimumab), Raptiva® (efalizumab), Remicade® (Infliximab), ReoPro® (Abciximab), Simulect® (Basiliximab), Synagis® (Palivizumab), Xolair® (Omalizumab), Zenapax® (Daclizumab), Zevalin® (Ibritumomab Tiuxetan), or Mylotarg® (gemtuzumab ozogamicin), receptors or soluble receptors, enzymes, variants, derivatives, or analogs of any of these antibodies.

Peptibodies, molecules comprising an antibody Fc domain attached to at least one antigen-binding peptide, are generally described in PCT publication WO 00/24782, published May 4, 2000. Immunoglobulin-like proteins, members of the immunoglobulin superfamily, contain one or more immunoglobulin-like domains which fold in structures similar to portions of the antibody variable region.

Exemplary protein concentrations in the formulation may range from about 0.1 mg/ml to about 180 mg/ml, about 0.3 mg/mL to about 150 mg/mL, from about 0.1 mg/mL to about 50 mg/mL, or from about 0.5 mg/mL to about 25 mg/mL, or alternatively from about 1 mg/mL to about 10 mg/mL. The concentration of protein will depend upon the end use of the pharmaceutical formulation and can be easily determined by a person of skill in the art. Particularly contemplated concentrations of protein are at least about 1.0, 1.5, 2.0, 2.5, 3.0, 3.5, 4.0, 5.0, 6.0, 7.0, 8.0, 9.0, 10.0, 15.0, 20.0, 25.0, 30.0, 35.0, or 40.0, or up to about 15.0, 20.0, 25.0, 30.0, 35.0, 40.0, 45.0, 50.0, 55.0, 60.0, 65.0, 70.0, 75.0, 80.0, 85.0, 90.0, 95.0, 100.0, 105.0, 110.0, 115.0, 120.0, 125.0, 130.0, 140.0 or 150.0 mg/mL.

As used herein, a "preservative" is an antimicrobial agent that kills or inhibits growth of microbes, including bacteria or yeast/fungi or other microorganisms. A preservative is generally present at a concentration that retards bacterial growth or contamination of drug products. Many preservatives are destabilizing to various degrees. Examples of destabilizing preservatives include, but are not limited to, benzyl alcohol, benzalkonium chloride, phenol, m-cresol, methyl p-hydroxybenzoate, benzoic acid, phenoxyethanol, methyl paraben, and propyl paraben and combinations of any of the above. Preferred preservatives which were observed to produce the least amount of destabilizing effect are benzyl alcohol and benzalkonium chloride.

Concentrations of destabilizing preservatives in a pharmaceutical formulation of the present invention are between about 0.001 M to about 0.15 M. Particularly contemplated concentrations of destabilizing preservatives include at least about 0.005, 0.01, 0.015, 0.02, 0.025, 0.03. 0.035, 0.04, 0.045, 0.05, 0.055, 0.06, 0.065, 0.07, 0.075, 0.08, 0.085, 0.09, or 0.095, or up to about, 0.04, 0.045, 0.05, 0.055, 0.06, 0.065, 0.07, 0.075, 0.08, 0.085, 0.09, 0.095, 0.10, 0.105, 0.11, 0.115, 0.12, 0.125, 0.13, 0.135, 0.14, or 0.145 M.

As used herein, "osmolytes" are low molecular weight organic compounds with no net charge. These include zwitterionic compounds (compounds that contain charged species, but whose overall charge is zero due to equal numbers of positive and negative charges). Examples of osmolytes contemplated for use in the present invention include, but are not limited to, sugars (e.g., sucrose, glucose, trehalose, fructose, xylose, mannitose, fucose), polyols (e.g., glycerol, mannitol, sorbitol, glycol, inositol), zwitterionic compounds (e.g., taurine), free amino acids with no net charge (e.g., glycine, proline, valine, leucine, alanine, glutamine), derivatives of amino acids (e.g., glycine betaine, alternatively referred to as betaine), and trimethylamino N-oxide (TMAO). Betaine, betaine derivatives, and TMAO are examples of zwitterionic tetra-substituted amine derivatives, which are also contemplated as osmolytes for use in the disclosed formulations. The osmolytes can optionally exclude glycine.

"Low molecular weight" encompasses any compound having a molecular weight less than about 1000, preferably less than about 750, more preferably less than about 500, and most preferably less than about 300 Da.

Concentrations of osmolytes in a pharmaceutical formulation of the present invention are between about 0.35 M and about 6 M. Also contemplated are concentrations of about 0.20 to about 6 M. Particularly contemplated concentrations are between about 0.50 M and about 5.5 M. Also contemplated are concentrations of osmolyte of at least about 0.20, 0.25, 0.30, 0.35, 0.40, 0.45, 0.55, 0.60, 0.65, 0.70, 0.75, 0.80, 0.85, 0.90, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, 5.0, 5.05, 5.1, 5.15, 5.2, 5.25, or 5.3 M, or concentrations of up to about 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, 5.0, 5.05, 5.1, 5.15, 5.2, 5.25, 5.3, 5.35, 5.4, 5.45, 5.5, 5.55, 5.6, 5.65, 5.7, 5.75, 5.8, 5.85, 5.9, or 5.95 M.

Exemplary molar ratios of concentration of osmolyte to destabilizing preservative of the present invention are between about 10:1 to about 175:1. Particularly contemplated ratios of osmolyte to destabilizing preservative are at least about or up to about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, or 29:1, 30:1, 31:1, 32:1, 33:1, 34:1, 35:1, 36:1, 37:1, 38:1. 39:1, 40:1, 41:1. 42:1, 43:1. 44:1, 45:1, 46:1, 47:1, 48:1, 49:1, 50:1, 55:1, 60:1. 65:1, 70:1, 75:1, 80:1, 85:1, 90:1, 95:1, 100:1, 110:1, 120:1, 130:1, 140:1, 150:1, or 160:1.

Exemplary molar ratios of osmolyte (M) to protein (mg/mL) of the present invention are between about 1:500 to about 60:1. Particularly contemplated ratios of osmolyte to protein are at least about or up to about 1:500, 1:400, 1:300, 1:250, 1:200, 1:150, 1:100, 1:95, 1:90, 1:85, 1:80, 1:75, 1:70, 1:65, 1:60, 1:55, 1:50, 1:45, 1:40, 1:35, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 35:1, 40:1, 45:1, 50:1, 55:1, or 60:1.

The stable formulations of protein, destabilizing preservative and osmolyte have longer shelf lives than preservative-containing formulations of proteins that do not contain sufficient osmolyte. Many package inserts for lyophilized protein formulations which are reconstituted with preservative-containing solutions specify that the shelf life at 2-8° C. is no longer than 28 days (4 weeks). The inclusion of an osmolyte according to the present invention results in a longer shelf life at 2-8° C., for example, at least 1 month, 2 months, 3 months, 6 months, 9 months, 1 year, 18 months or 2 years, and also results in a longer shelf life at other temperatures, such as 25-30° C. (room temperature).

As used herein, "shelf life" means that the storage period during which an active ingredient such as a therapeutic protein in a pharmaceutical formulation has minimal degradation (e.g., not more than about 2-3% degradation) when the pharmaceutical formulation is stored under specified storage conditions, for example, 2-8° C. Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. The pharmaceutical formulations of the present invention preferably exhibit degradation (e.g., fragmentation, aggregation or unfolding) of not more than about 2 to about 3% over two years when stored at 2-8° C.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The following formulations were prepared and studied for their stability. In particular, the change of circular dichroism (CD) signal at 290 or 295 nm in the CD spectra of these formulations as a function of temperature was used to determine the stability of the protein in the presence of different amounts of preservative and osmolyte. CD signal at 290 or 295 nm originates primarily from aromatic amino acids such as tyrosine and tryptophan residues of proteins. In general, proteins containing aromatic amino acids with well defined tertiary structures give rise to sharp CD signals at 290 or 295 nm due to the chirality of aromatic side chains. However, the CD signal at 290 or 295 nm usually decreases dramatically when the tertiary structure of a protein unfolds at higher temperatures and the conformational flexibility of the aromatic side chains increases.

All data were collected on a Jasco CD (Model J-810, Serial # B038260750) spectrometer under the following parameters: band width-1 nm; response-16 sec; sensitivity-standard; measurement range-20 to 95° C.; data pitch-0.2° C.; monitor wavelength-295 nm; temperature slope-1° C./min; and cell length-1 cm.

Example 1

Darbepoetin

Recombinantly produced bulk Darbepoetin was concentrated to 10 mg/mL using centriprep 10 K centrifugal concentrators. Formulations used in the experiment were with 0.6 mL of the bulk solution (for 2 mg/mL final concentration of Darbepoetin), 20 mM sodium phosphate, 100 mM sodium chloride and at a pH of 6.90.

Formulations

A. Assessment of Preservatives for Destabilizing Effect with Darbepoetin

Five formulations with different destabilizing preservatives were prepared. All formulations contained 1.0 mg/mL Darbepoetin, 20 mM sodium phosphate, 140 mM sodium chloride, and were at a pH of 6.00. Concentrations of destabilizing preservatives were as follows: 0.5% phenol (0.057 M), 0.5% sodium benzoate (0.035 M), 0.5% m-cresol (0.048 M), and 0.5% benzyl alcohol (0.048 M). The CD spectrum of each formulation was observed at 290 nm from 5 to 80° C. and compared against a control formulation with no preservative. The order of the denaturing effect of these preservatives was, from least destabilizing to most destabilizing, sodium benzoate, benzyl alcohol, phenol, and m-cresol.

B. Assessment of Destabilizing Effect of Benzyl Alcohol at Various Concentrations with Darbepoetin Seven formulations of Darbepoetin with benzyl alcohol were prepared. All formulations contained 1.0 mg/mL Darbepoetin, 150 mM sodium phosphate, 70 mM sodium chloride and were at a pH of 6.00. The concentration of benzyl alcohol in each formulation was varied as follows: 0.1% (0.010 M), 0.3% (0.029 M), 0.5% (0.049 M), 0.7% (0.068 M), 1.0% (0.097 M), 1.2% (0.117 M), and 1.5% (0.146 M). The thermal stability of Darbepoetin in each formulation was monitored by the CD signal at 290 nm over a temperature range of 5 to 80° C. and compared against a control formulation with no benzyl alcohol. The thermal stability of Darbepoetin decreased as the concentration of benzyl alcohol increased. Benzyl alcohol had a linear and non-cooperative effect on the thermal stability of Darbepoetin tertiary structure.

The effect that benzyl alcohol has on the secondary structure of Darbepoetin was also investigated. Six formulations of differing concentrations of benzyl alcohol [1.0% (0.097 M), 1.2% (0.117 M), 1.4% (0.136 M), 1.6% (0.155 M), 1.8% (0.175 M) and 2.0% (0.194 M)] in 1.0 mg/mL Darbepoetin, 10 mM sodium phosphate, 150 mM sodium chloride, at a pH of 6.0 were produced and their Fourier Transform Infrared (FTIR) spectra measured. The second derivative FTIR spectra in the amide I region (1600-1700 $cm^{-1}$) are sensitive to change in the secondary structures of Darbepoetin. The FTIR spectra of these formulations showed no significant spectral change at benzyl alcohol concentrations up to 1.4% (0.136 M), suggesting that there is no significant change in the secondary structure of Darbepoetin at benzyl alcohol concentrations below 1.4% (0.136 M). At benzyl alcohol concentrations of 1.6% (0.155M) and above, there appears to be an increase in the concentration of unfolded protein as evidenced by an increase in the IR intensity at 1622 and 1635 $cm^{-1}$.

C. Darbepoetin Formulations with 1.5% (0.145 M) Benzyl Alcohol and 1 M of Various Osmolytes The effect of osmolyte on the tertiary structure of Darbepoetin in the presence of 1.5% (0.145 M) benzyl alcohol was investigated to determine if osmolytes can counteract the unfolding effect of benzyl alcohol. The melting transition of Darbepoetin (1.0 mg/mL) in the presence of 1.5% (0.145 M) benzyl alcohol, 150 mM sodium phosphate, 70 mM sodium chloride at a pH of 6.00 and one of the following: 1M glycine, 1M TMAO, or 1M proline. CD spectra of the three formulations were measured at 290 nm over temperatures from 5 to 80° C. and compared against a control formulation with 1.5% (0.145 M) benzyl alcohol and no osmolyte. Both 1M TMAO and 1M proline stabilized the Darbepoetin against benzyl alcohol denaturation. TMAO appeared to be more effective than proline, while 1M glycine destabilized Darbepoetin stability.

D. Darbepoetin Formulations with 1.0% (0.097 M) Benzyl Alcohol and Various Concentrations of Glycerol Formulations of 1.0 mg/mL Darbepoetin in 150 mM sodium phosphate, 70 mM sodium chloride, and at a pH of 6.00 were prepared with varying amounts of glycerol as osmolyte. Three different concentrations of glycerol were assessed: 10% (1.357 M), 20% (2.714 M) and 40% (5.428 M) by monitoring the CD spectra at 290 nm from 5 to 80° C. and compared against a control formulation with 1.0% (0.097 M) benzyl alcohol and no osmolyte. The thermal transition of the tertiary structure of Darbepoetin in 1% (0.097 M) benzyl alcohol was increased significantly with increasing amounts of glycerol.

E. Darbepoetin with 1.5% (0.145 M) Benzyl Alcohol and with or without 20% (2.714 M) Glycerol The effect of 20% (2.714 m) glycerol on the thermal stability of a formulation of 1.0 mg/mL Darbepoetin in 150 mM sodium phosphate, 70 mM sodium chloride at a pH of 6.00 with 1.5% (0.145 M) benzyl alcohol was assessed. As shown by the CD signal at 290 nm, the tertiary structure of Darbepoetin in a formulation containing 1.5% (0.145M) benzyl alcohol is almost completely unfolded at room temperature. The addition of 20% (2.714 M) glycerol restored most of the unfolded tertiary structure of Darbepoetin in the present of 1.5% (0.145 M) benzyl alcohol at room temperature.

F. Darbepoetin with 0.1% (0.009 M) Benzalkonium Chloride with and without 40% (5.428 M) Glycerol Two formulations were prepared with 2 mg/mL Darbepoetin, 20 mM sodium phosphate, 100 mM sodium chloride at a pH of 6.90. One was prepared with 40% (5.428 M) glycerol and the other was prepared with no osmolyte. The stability of the Darbepoetin was assessed by measuring the CD spectra at 290 nm over the temperature range of 4 to 70° C. FIG. 1 shows the CD spectra measured for these three different formulations. The benzalkonium chloride significantly destabilized the Darbepoetin, but the addition of 40% (5.428 M) glycerol significantly stabilized the Darbepoetin in the presence of the benzalkonium chloride, and actually increased the melting temperature of the Darbepoetin to higher than that in a formulation without benzalkonium chloride.

Example 2

Leptin

Formulations

A. Control Formulation

A formulation is prepared containing sodium acetate, water, and leptin at a final concentration of 0.5 mg/mL, with a pH between 4 and 5. This formulation serves as the control solution having neither osmolyte nor destabilizing preservative.

A second control formulation is prepared containing sodium acetate, water, benzyl alcohol, and leptin at a final concentration of 0.5 mg/mL, pH 4-5. This formulation serves as the control solution having no osmolyte, but with a destabilizing preservative.

B. Formulations of Leptin with 1% benzyl alcohol or 0.02% benzalkonium chloride and glycerol, sarcosine, or sucrose A formulation of 20% glycerol, 1% benzyl alcohol, and 0.5 mg/mL leptin is prepared by mixing sodium acetate, water, glycerol, benzyl alcohol, and bulk solution of leptin and adjusting the pH to between 4 and 5.

A formulation of 500 mM sarcosine, 1% benzyl alcohol, and 0.5 mg/mL leptin is prepared by mixing sodium acetate, water, sarcosine solution, benzyl alcohol, and bulk protein solution of leptin and adjusting the pH to between 4 and 5.

A formulation of 300 mM sucrose, 1% benzyl alcohol, and 0.5 mg/mL leptin is prepared by mixing sodium acetate, water, sucrose solution, benzyl alcohol, and bulk protein solution of leptin and adjusting the pH to between 4 and 5.

A formulation of 20% glycerol, 0.02% benzalkonium chloride, and 0.5 mg/mL leptin is prepared by mixing sodium acetate, water, glycerol solution, benzalkonium chloride solution, and bulk protein solution of leptin and adjusting the pH to between 4 and 5.

C. Stability Assessment

The CD spectra of the formulations described above are measured over a range of temperatures to assess the stability of the leptin in the formulation. HPLC is used to assess the level of degradation and/or aggregation of the protein in the various formulations prepared.

Example 3

GCSF

Formulations

A. Control Formulation

A formulation was prepared containing sodium acetate, water, and GCSF at a final concentration of 3 mg/mL, and a pH of 4. This formulation serves as the control solution having neither osmolyte nor destabilizing preservative.

A second control formulation was prepared containing sodium acetate, water, benzyl alcohol (1% or 0.097 M), and GCSF at a final concentration of 3 mg/mL, and a pH of 4. This formulation serves as the control solution having no osmolyte, but with a destabilizing preservative.

B. Formulations of GCSF with benzyl alcohol and sorbitol, glycerol, or sarcosine A formulation of 10% (0.549 M) sorbitol, 1% benzyl alcohol and _ mg/mL GCSF was prepared and adjusted to a pH 4.00.

A formulation of 10% (1.357 M) glycerol, 1% (0.097 M) benzyl alcohol, and 3 mg/mL GCSF was prepared and adjusted to a pH of 4.00.

A formulation of 500 mM sarcosine, 1% (0.097 M) benzyl alcohol, and 3 mg/mL GCSF was prepared and adjusted to a pH of 4.00.

A formulation of 10% (0.3 M) sucrose, 1% benzyl alcohol, and 1 mg/mL GCSF is prepared by mixing sodium acetate, water, sucrose solution, benzyl alcohol solution, and bulk protein solution of GCSF, with the pH adjusted to about 4.

A formulation of 20% glycerol, 0.02% (0.002 M) benzalkonium chloride, and 1 mg/mL GCSF is prepared by mixing sodium acetate, water, glycerol solution, benzalkonium chloride, and bulk protein solution of GCSF, with the pH adjusted to about 4.

C. Stability Assessment

Figure 2:
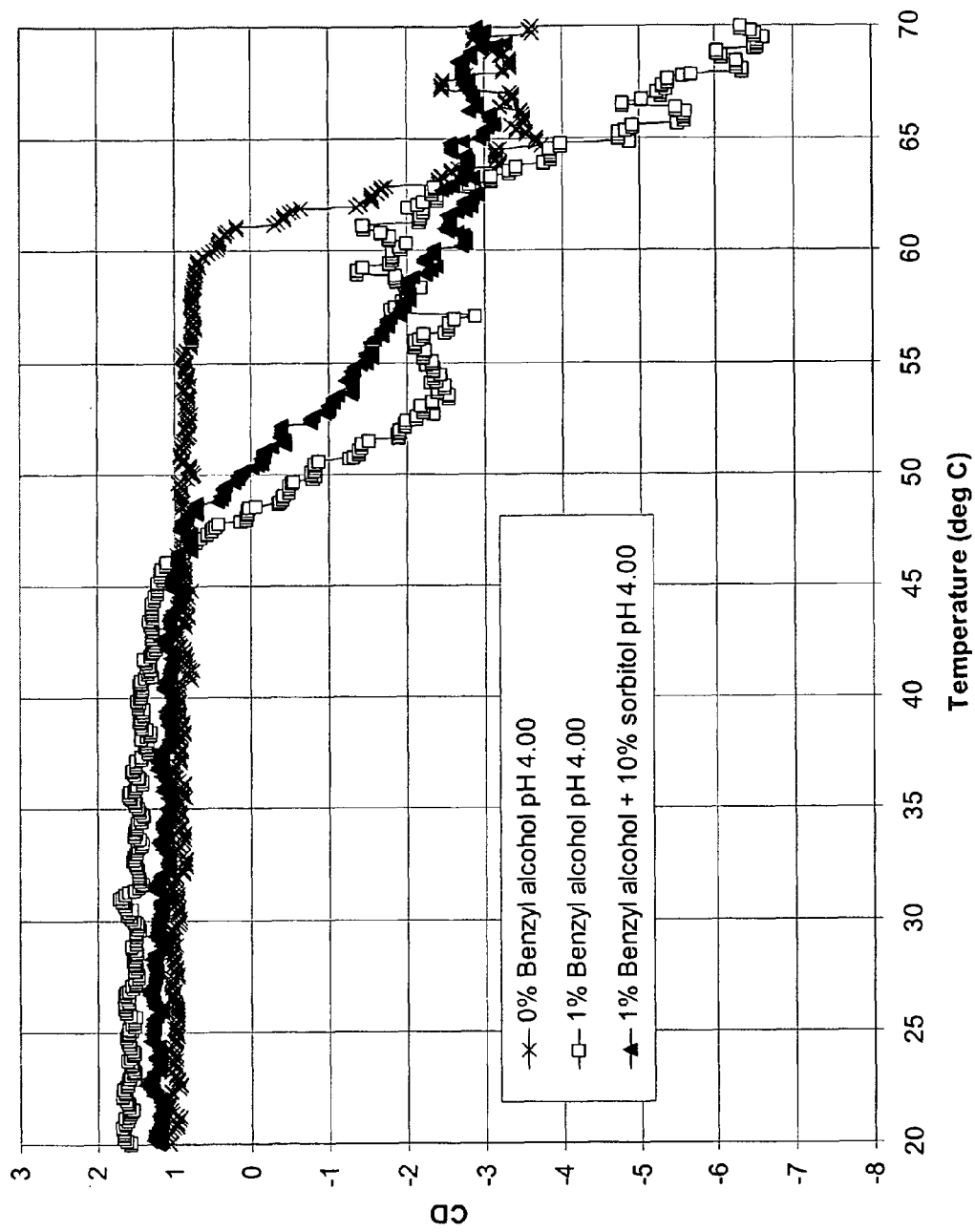
FIG. 2 is a graph displaying the effect of sorbitol (10% or 0.549 M) and benzyl alcohol (1% or 0.097 M) on the stability of GCSF in a formulation at pH 4.00.
Figure 3:
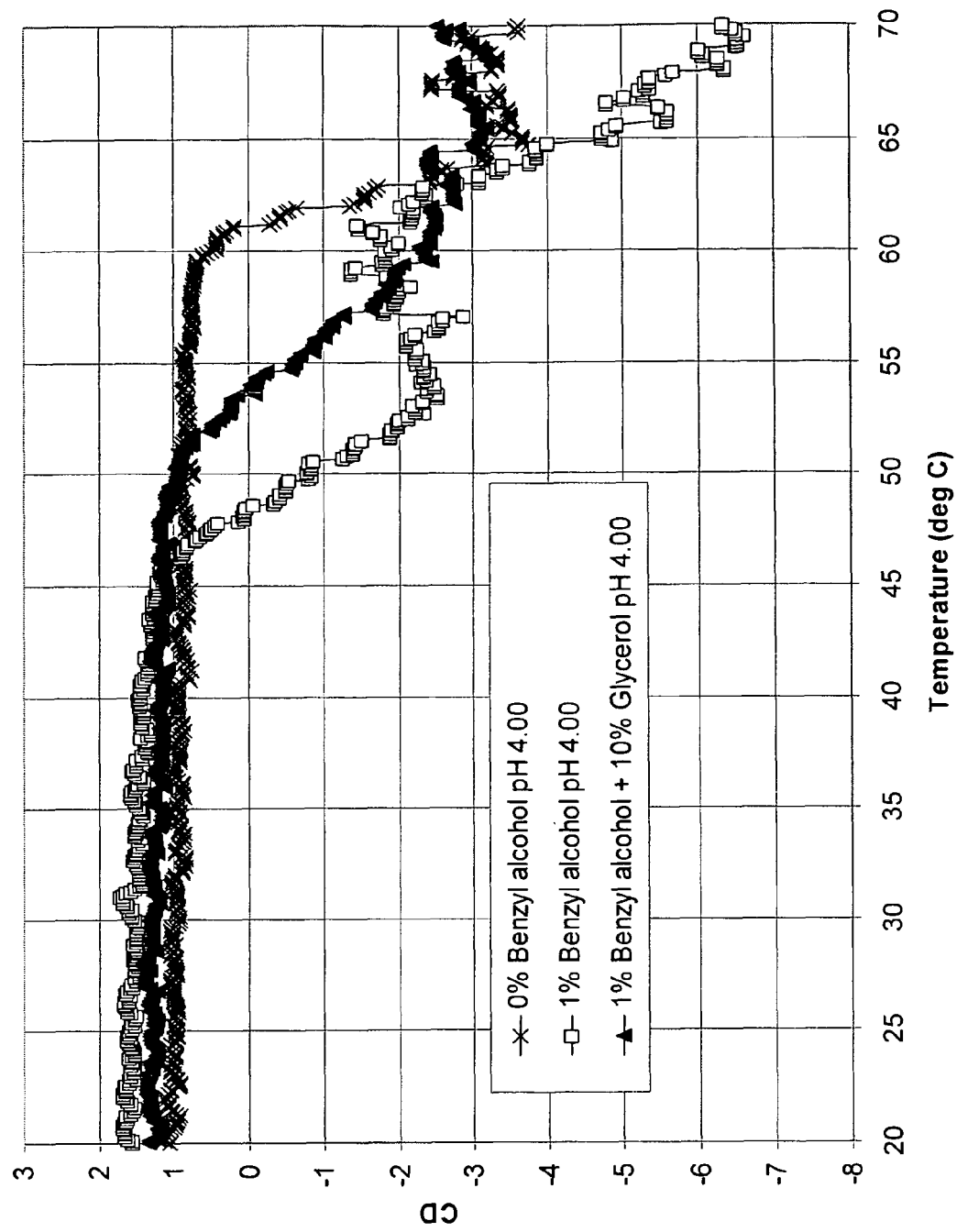
FIG. 3 is a graph displaying the effect of glycerol (10% or 1.357 M) and benzyl alcohol (1% or 0.097 M) on the stability of GCSF in a formulation at pH 4.00.
Figure 4:
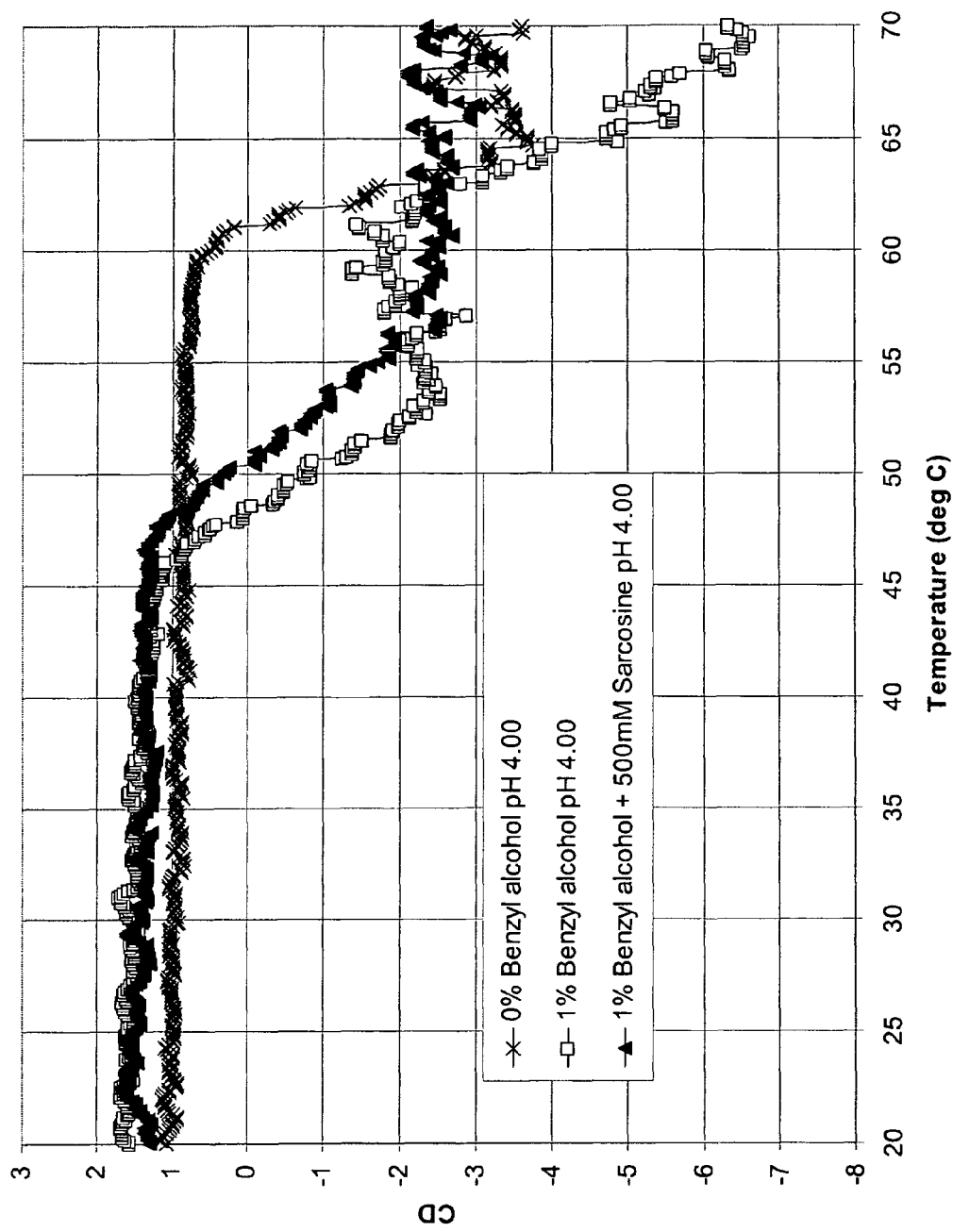
FIG. 4 is a graph displaying the effect of sarcosine (500 mM) and benzyl alcohol (1% or 0.097 M) on the stability of GCSF in a formulation at pH 4.00.
Figure 5:
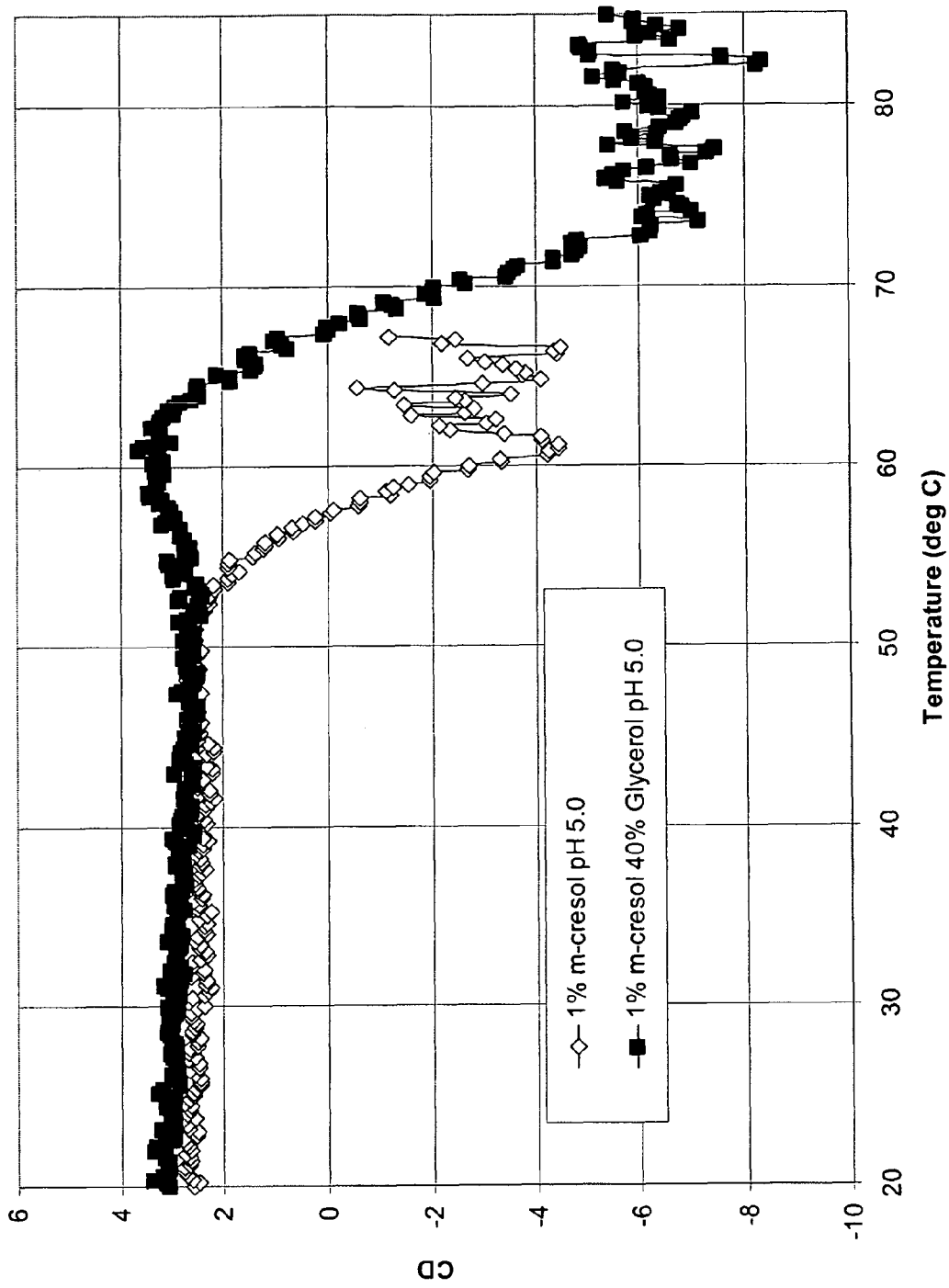
FIG. 5 is a graph displaying the effect of 40% (5.428 M) glycerol and m-cresol (1% or 0.009 M) on the stability of anti-streptavidin in a formulation.

The CD spectra of the formulations described above are measure over a range of temperatures to assess the stability of the GCSF in the formulation. The CD spectra for the near UV CD spectra of the formulations having 10% sorbitol, 10% glycerol, and 500 mM sarcosine in comparison with the formulations having no preservative or osmolyte and no osmolyte are shown in FIGS. 2, 3, and 4. HPLC is used to assess the level of aggregation and/or degradation of the protein in the formulations prepared.

Example 4

Anti-Streptavidin Fully Human IgG2

Ten mL of a 20 mg/mL stock solution of anti-streptavidin IgG2 antibody was dialyzed overnight at 4° C. in 2 L of 20 mM sodium acetate at pH 5.00 in order to remove sorbitol from the bulk solution. The formulations used in the experiments were with 2 mg/mL anti-streptavidin, 20 mM sodium acetate and at a pH of 5.00. The various preservatives and osmolytes were added and vortexed to mix.

Formulations

A. Control Formulations

A formulation was prepared from 0.6 mL of 100 mM sodium acetate, 2.1 mL water, and 0.3 mL of the bulk protein solution of anti-streptavidin described above. This formulation served as the control solution having neither osmolyte nor destabilizing preservative.

A second control formulation was prepared from 0.6 mL 100 mM sodium acetate, 2.07 mL water, 0.030 mL benzyl alcohol, and 0.3 mL of the bulk protein solution of anti-streptavidin described above. This formulation served as the control solution having no osmolyte, but with a destabilizing preservative.

B. Formulations of Anti-Streptavidin with Benzyl Alcohol and Various Osmolytes

A formulation of 10% (1.357 M) glycerol, benzyl alcohol, and anti-streptavidin was prepared by mixing 0.6 mL sodium acetate, 1.47 mL water, 0.6 mL of a 50% glycerol solution, 0.03 mL benzyl alcohol, and 0.3 mL of the bulk protein solution of anti-streptavidin described above.

A formulation of 1M sarcosine, benzyl alcohol, and anti-streptavidin was prepared by mixing 0.6 mL sodium acetate, 0.57 mL water, 1.5 mL of a 2M sarcosine solution, 0.03 mL benzyl alcohol, and 0.3 mL of the bulk protein solution of anti-streptavidin described above. The 2 M sarcosine stock solution used in the formulations was prepared in water and the pH adjusted to 5.00 by titrating with glacial acetic acid.

A formulation of 200 mM sarcosine, benzyl alcohol, and anti-streptavidin was prepared by mixing 0.6 mL sodium acetate, 1.77 mL water, 0.3 mL of a 2M sarcosine solution, 0.03 mL benzyl alcohol, and 0.3 mL of the bulk protein solution of anti-streptavidin described above.

A formulation of 100 mM sarcosine, benzyl alcohol, and anti-streptavidin was prepared by mixing 0.6 mL sodium acetate, 1.92 mL water, 0.15 mL of a 2M sarcosine solution, 0.03 mL benzyl alcohol, and 0.3 mL of the bulk protein solution of anti-streptavidin described above.

A formulation of 1M proline, benzyl alcohol, and anti-streptavidin was prepared by mixing 0.6 mL sodium acetate, 0.57 mL water, 1.5 mL of a 2M proline solution, 0.03 mL benzyl alcohol, and 0.3 mL of the bulk protein solution of anti-streptavidin described above. The 2 M proline solution used in this formulation was prepared in water and the pH adjusted to 5.0 by titrating with glacial acetic acid.

A formulation of 10% (0.549 M) sorbitol, benzyl alcohol, and anti-streptavidin was prepared by mixing 0.6 mL sodium acetate, 1.425 mL water, 0.375 mL of a 80% sorbitol solution, 0.03 mL benzyl alcohol, and 0.3 mL of the bulk protein solution of anti-streptavidin described above. The 80% sorbitol solution used in the formulations was prepared in water.

A formulation of 40% (2.195 M) sorbitol, benzyl alcohol, and anti-streptavidin was prepared by mixing 0.6 mL sodium acetate, 0.57 mL water, 1.50 mL of a 80% sorbitol solution, 0.03 mL benzyl alcohol, and 0.3 mL of the bulk protein solution of anti-streptavidin described above.

A formulation of 1M sucrose, benzyl alcohol, and anti-streptavidin was prepared by mixing 0.6 mL sodium acetate, 0.57 mL water, 1.5 mL of a 2M sucrose solution, 0.03 mL benzyl alcohol, and 0.3 mL of the bulk protein solution of anti-streptavidin described above. The 2M sucrose solution used in the formulations was prepared in water.

All of the above formulations were assessed for anti-streptavidin stability by monitoring the CD spectra at 290 at a temperature range from 20 to 90° C.

Figure 8:
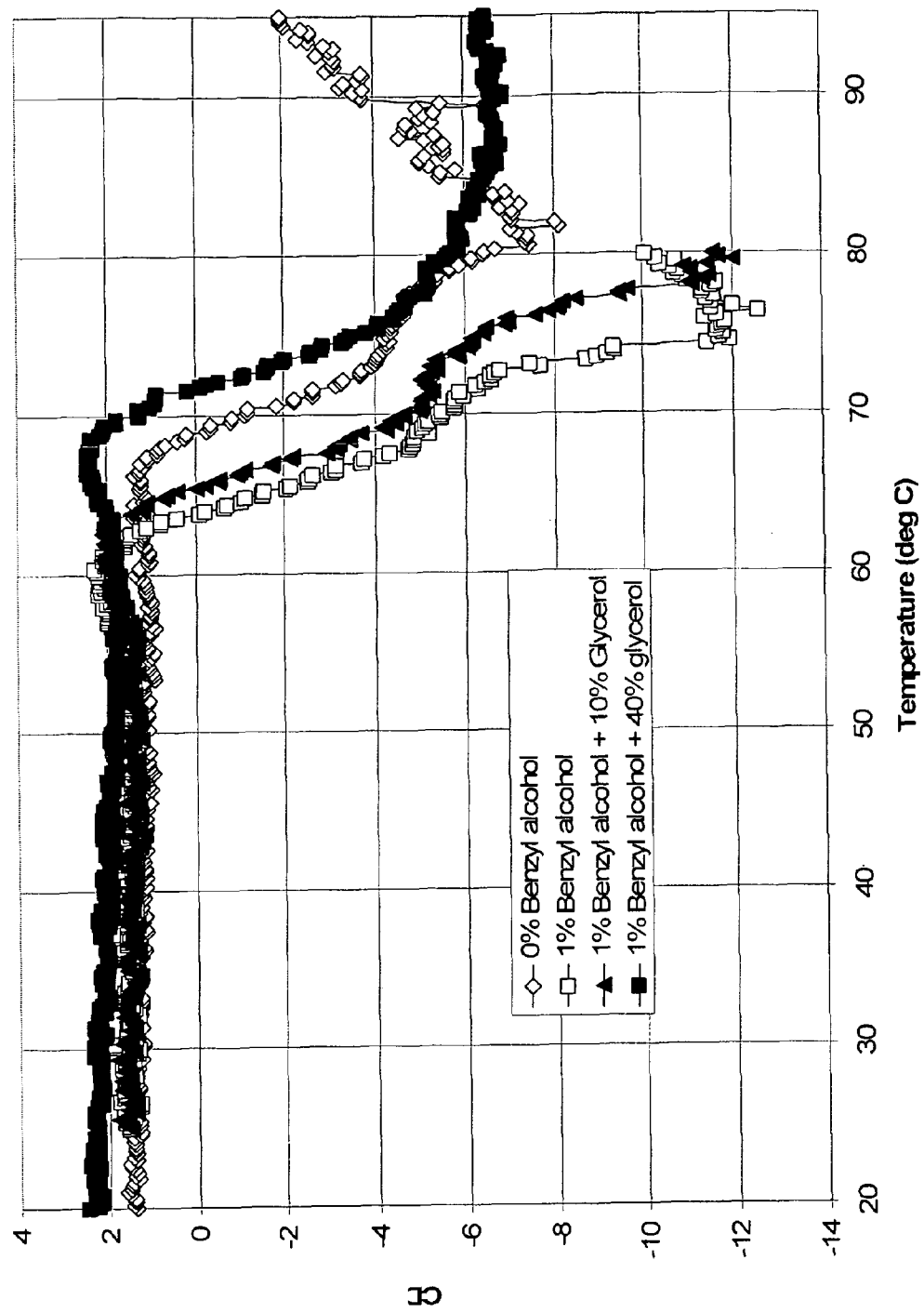
FIG. 8 is a representative graph displaying the effect of the destabilizing preservative benzyl alcohol on the stability of the antibody anti-streptavidin in the absence of any osmolyte and in the presence of 10% and 40% glycerol, as measured using circular dichroism (CD).

The anti-streptavidin antibody unfolds in two transitions. The second transition, leading to insoluble aggregation, is destabilized by benzyl alcohol to a greater extent than the first transition is. However, the second transition is stabilized by glycerol to a greater extent than the first transition is. The formulation containing 1% (0.097 M) benzyl alcohol and 40% (5.428 M) glycerol is more thermally stable than the formulation without benzyl alcohol (see FIG. 8). The addition of 40% (5.428 M) glycerol to the antibody solution stabilizes the antibody at high temperatures and prevents precipitation from occurring.

Sarcosine was beneficial in stabilizing the anti-streptavidin antibody. However, its effects were less than the stability achieved from the addition of glycerol. Sarcosine's effects were seen at as low a concentration as 100 mM, albeit at a small amount. Proline was unable to stabilize the anti-streptavidin antibody and actually destabilized it, lowering its melting temperature. Sorbitol stabilized the anti-streptavidin antibody. Higher concentrations of sorbitol were more beneficial than lower. However, unlike glycerol, it was unable to prevent the precipitation of the antibody at temperatures above 80° C. Sucrose (1 M) was able to significantly increase the melting temperature of the anti-streptavidin antibody in the presence of 1% (0.097 M) benzyl alcohol. The effect of 1M sucrose was more effective on the first unfolding transition of the antibody than on the second unfolding transition.

C. Formulation of Anti-Streptavidin with m-Cresol and 40% Glycerol

A formulation of the antibody anti-streptavidin (3 mg/mL) with 1% (0.009M) m-cresol and 40% (5.428M) glycerol were mixed together to form a stable aqueous solution at pH5. The CD spectrum of the formulation was measured and compared against that of a formulation of anti-streptavidin (3 mg/mL) and 1% (0.009M) m-cresol at pH 5.00 without any osmolyte to assess the effect the osmolyte has on the stability of the protein in the formulation. What was found was that the 40% (5.428M) glycerol significantly increased the stability of the anti-streptavidin antibody in the pharmaceutical formulation (see FIG. 8).

D. Formulations of Anti-Streptavidin with Paraben and Glycerol

A formulation of the antibody anti-streptavidin (3 mg/mL) with paraben (methyl or propyl or a mixture) (0.1% or 0.007 M) and glycerol (between 10-20% or 1.357 to 2.714 M) are mixed together to form a stable aqueous solution. The CD spectrum of the formulation is measured and compared against that of a formulation of anti-streptavidin and paraben without any osmolyte to assess the effect the osmolyte has on the stability of the protein in the formulation.

E. Formulations of Anti-Streptavidin with Benzyl Alcohol and TMAO

Figure 6:
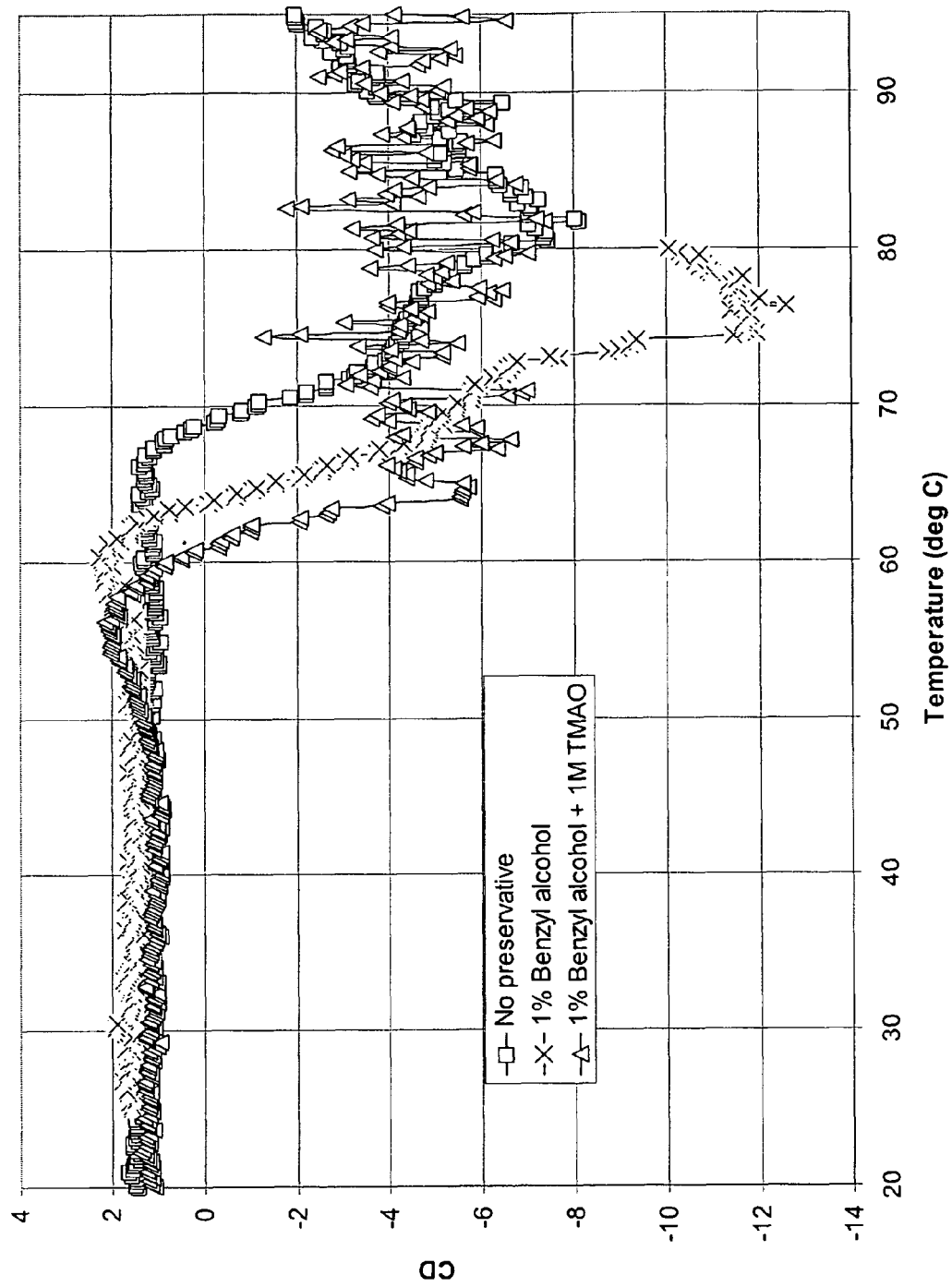
FIG. 6 is a graph displaying the effect of TMAO (1M) and benzyl alcohol (1% or 0.097 M) on the stability of anti-streptavidin in a formulation at pH 5.00.
Figure 7:
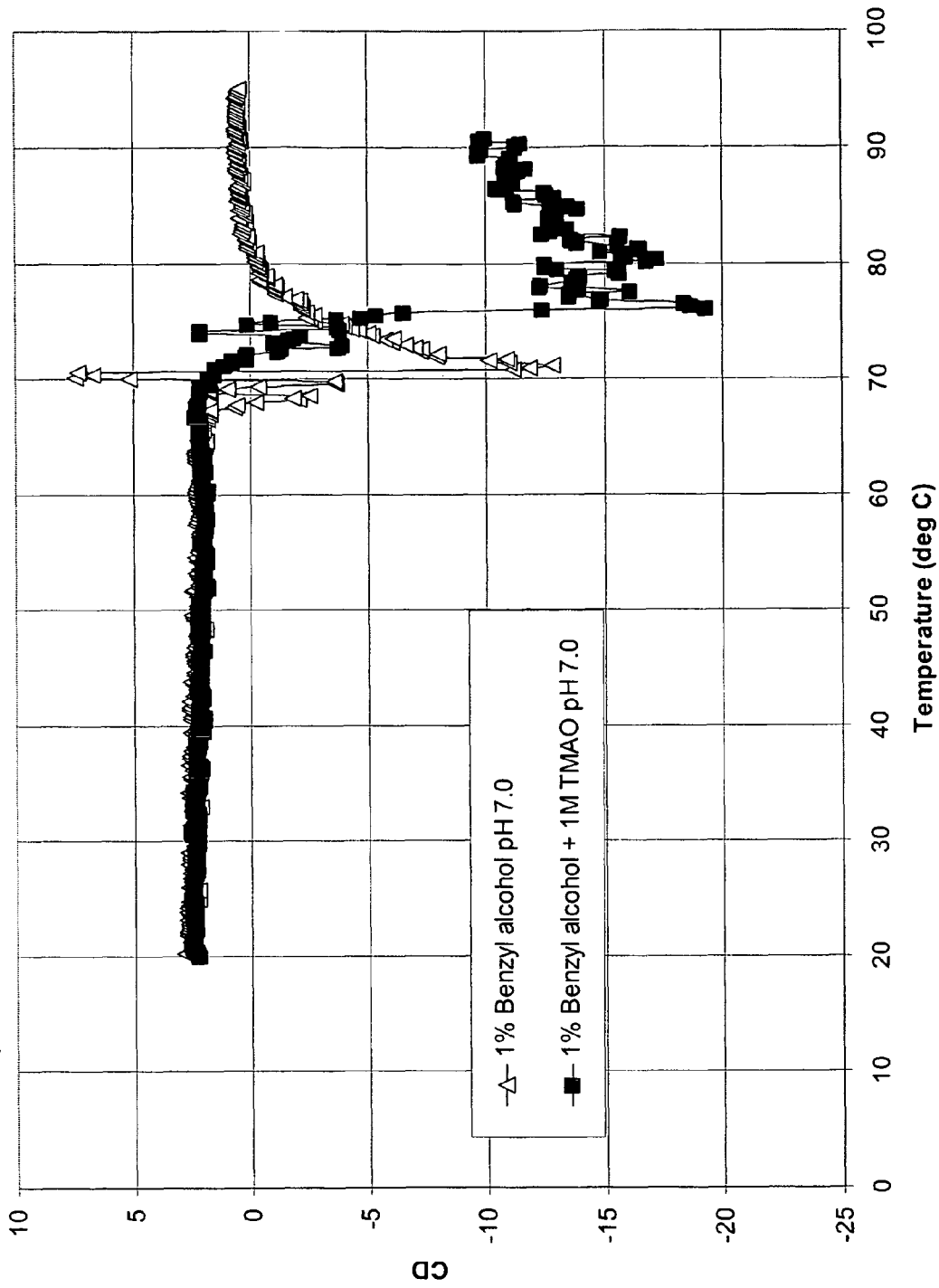
FIG. 7 is a graph displaying the effect of TMAO (1M) and benzyl alcohol (1% or 0.097 M) on the stability of anti-streptavidin in a formulation at pH 7.00.

Formulations of anti-streptavidin (2 mg/mL) and sodium acetate (20 mM) at pH 5.00 were prepared with no TMAO or benzyl alcohol, with benzyl alcohol (1% or 0.097 M), and with benzyl alcohol (1% or 0.097 M) and TMAO (1M). The stability was measured by monitoring the CD spectrum at 295 nm over a temperature range of 50 to 90° C. TMAO was a destabilizing additive to the formulation at a pH 5.00 (FIG. 6). Since TMAO possesses an ionizable group with a pKa of about 4.60, it is postulated, though not relied upon, that there is an appreciable amount of ionized TMAO in the protein formulation at pH 5.00, and that TMAO is better at stabilizing protein formulations at higher pHs, e.g., 6.00 or above. This conclusion is exemplified by the stability study of anti-streptavidin formulations at pH 7.00, wherein 1 M TMAO was able to stabilize the anti-streptavidin (FIG. 7).

E. Stability of Anti-Streptavidin Formulations Over Time

To assess the effect of a destabilizing preservative and an osmolyte on the denaturation of anti-streptavidin over time, several formulations were prepared and stored at 52° C. for one week. After one week, the formulations were analyzed using SEC-HPLC to measure the concentration of aggregate—the less aggregate formed, the more stable the formulation for the anti-streptavidin antibody.

All the formulations were prepared with the following components: a 2 mg/mL concentration of antistreptavidin, 20 mM sodium acetate, pH of 5.00. Three variants were made: 1) a formulation further containing 1% (0.097 M) benzyl alcohol; 2) a formulation further containing 1% (0.097 M) benzyl alcohol and 10% (1.357 M) glycerol, and 3) a formulation further containing 1% (0.097 M) benzyl alcohol and 40% (5.428 M) glycerol).

After a week, the formulation with 1% (0.097M) benzyl alcohol but no glycerol contained 59% aggregate. The formulation with 10% (1.357 M) glycerol contained 24% aggregate while the one containing 40% (5.428 M) glycerol contained only 7% aggregate. These data show that the osmolyte is able to counteract, or mitigate, the concentration of unfolding due to the presence of the destabilizing preservative.

Example 5

Herceptin

Ten mLs of a 21 mg/mL Herceptin IgG1 humanized antibody containing histidine, trehalose, 1.1% benzyl alcohol, and Tween-20 was dialyzed overnight at 4° C. in 2 L of 20 mM sodium acetate at pH 5.00. The formulations used in the experiments were with 2 mg/mL Herceptin, 20 mM sodium acetate at a pH of 5.00.

Formulations

A. Control Formulations

A formulation was prepared from 0.6 mL of 100 mM sodium acetate, 2.1 mL water, and 0.3 mL of the bulk protein solution of Herceptin described above. This formulation served as the control solution having neither osmolyte nor destabilizing preservative.

A second control formulation was prepared from 0.6 mL 100 mM sodium acetate, 2.07 mL water, 0.030 mL benzyl alcohol, and 0.3 mL of the bulk protein solution of Herceptin described above. This formulation served as the control solution having no osmolyte, but with a destabilizing preservative.

B. Formulations of Herceptin with Benzyl Alcohol and Various Osmolytes

A formulation of 10% (1.357 M) glycerol, benzyl alcohol, and Herceptin was prepared by mixing 0.6 mL sodium acetate, 1.47 mL water, 0.6 mL of a 50% glycerol solution, 0.03 mL benzyl alcohol, and 0.3 mL of the bulk protein solution of Herceptin described above.

A formulation of 40% (5.428 M) glycerol, benzyl alcohol, and Herceptin was prepared by mixing 0.6 mL sodium acetate, 0.57 mL water, 1.5 mL of a 80% glycerol solution, 0.03 mL benzyl alcohol, and 0.3 mL of the bulk protein solution of Herceptin described above.

A formulation of 1 M TMAO, benzyl alcohol, and Herceptin was prepared by mixing 0.6 mL sodium acetate, 0.57 mL water, 1.5 mL of a 2M TMAO solution, 0.03 mL benzyl alcohol, and 0.3 mL of the bulk protein solution of Herceptin described above. The 2M TMAO solution was prepared in water and the pH adjusted to pH 5.00 by titrating with 6M hydrochloric acid.

Figure 9:
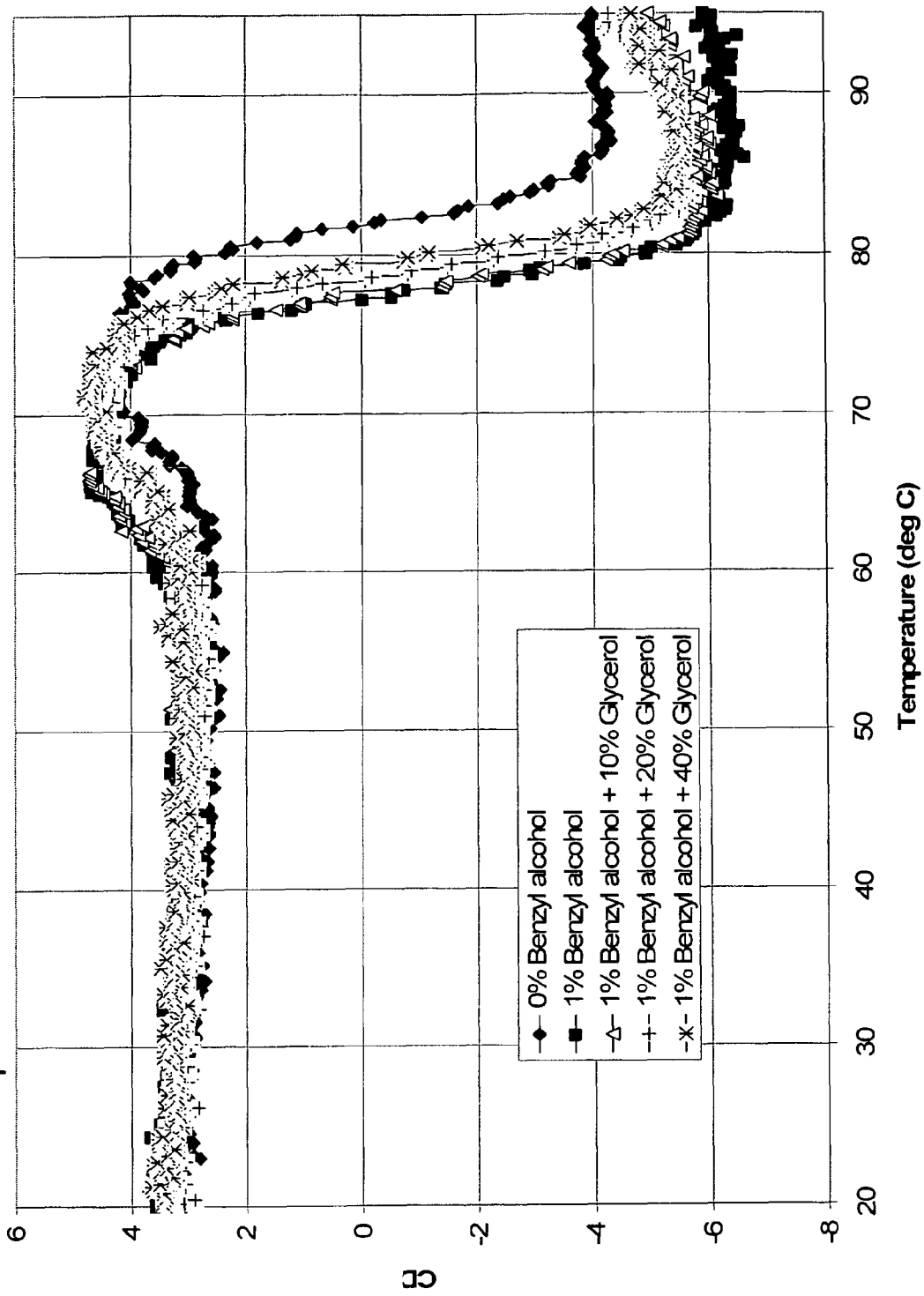
FIG. 9 is a representative graph displaying the effect of the destabilizing preservative benzyl alcohol on the stability of the antibody Herceptin® in the absence of any osmolyte and in the presence of 10%, 20%, or 40% glycerol, as measured using circular dichroism (CD).

Benzyl alcohol at 1% (0.097 M) destabilizes Herceptin (see FIG. 9). Addition of glycerol stabilizes Herceptin with increasing stability occurring with increasing amounts of glycerol from 10% (1.357 M) to 20% (2.714 M) to 40% (5.428 M).

Attempts to stabilize Herceptin using TMAO were unsuccessful. TMAO lowered the melting temperature of Herceptin and caused the antibody to precipitate out of solution.

Example 6

Rituxan

Ten mLs of Rituxan, a murine/human chimeric IgG 1 antibody at 10 mg/mL in sodium citrate, sodium chloride, Tween-80 at pH 6.50 was dialyzed in 2 L of 20 mM sodium acetate at pH 5.00 overnight at 4° C. The formulations used in the experiments were with 2 mg/mL Rituxan, 20 mM sodium acetate and at a pH of 5.00.

Formulations

A. Control Formulations

A formulation was prepared from 0.6 mL of 100 mM sodium acetate, 1.8 mL water, and 0.6 mL of the bulk protein solution of Rituxan described above. This formulation served as the control solution having neither osmolyte nor destabilizing preservative.

A second control formulation was prepared from 0.6 mL 100 mM sodium acetate, 1.77 mL water, 0.030 mL benzyl alcohol, and 0.6 mL of the bulk protein solution of Rituxan described above. This formulation served as the control solution having no osmolyte, but with a destabilizing preservative.

B. Formulations of Rituxan with Benzyl Alcohol and Various Osmolytes

A formulation of 10% (1.357 M) glycerol, benzyl alcohol, and Rituxan was prepared by mixing 0.6 mL sodium acetate, 1.17 mL water, 0.6 mL of a 50% glycerol solution, 0.03 mL benzyl alcohol, and 0.6 mL of the bulk protein solution of Rituxan described above.

A formulation of 40% (5.428 M) glycerol, benzyl alcohol, and Rituxan was prepared by mixing 0.6 mL sodium acetate, 0.27 mL water, 11.5 mL of a 80% glycerol solution, 0.03 mL benzyl alcohol, and 0.6 mL of the bulk protein solution of Rituxan described above.

A formulation of 1M TMAO, benzyl alcohol, and Rituxan was prepared by mixing 0.6 mL sodium acetate, 0.27 mL water, 1.5 mL of a 2M TMAO solution, 0.03 mL benzyl alcohol, and 0.6 mL of the bulk protein solution of Rituxan described above. The 2M solution of TMAO was prepared in water and adjusted to a pH of 5.00 by titrating with glacial acetic acid.

A formulation of 1M glycine, benzyl alcohol, and Rituxan was prepared by mixing 0.6 mL sodium acetate, 0.27 mL water, 1.5 mL of a 2M glycine solution, 0.03 mL benzyl alcohol, and 0.6 mL of the bulk protein solution of Rituxan described above. The 2M solution of glycine was prepared in water and the pH adjusted to 5.00 by titrating with glacial acetic acid.

A formulation of 200 mM glycine, benzyl alcohol, and Rituxan was prepared by mixing 0.6 mL sodium acetate, 1.47 mL water, 0.3 mL of a 2M glycine solution, 0.03 mL benzyl alcohol, and 0.6 mL of the bulk protein solution of Rituxan described above. The 2M solution of glycine was prepared in water and the pH adjusted to 5.00 by titrating with glacial acetic acid.

A formulation of 1M glycine, 10% (1.357 M) glycerol, benzyl alcohol, and Rituxan was prepared by mixing 0.27 mL sodium acetate, 0.6 mL water, 1.5 mL of a 2M glycine solution, 0.03 mL benzyl alcohol, and 0.6 mL of the bulk protein solution of Rituxan described above. The 2M solution of glycine was prepared in water and the pH adjusted to 5.00 by titrating with glacial acetic acid.

Figure 10:
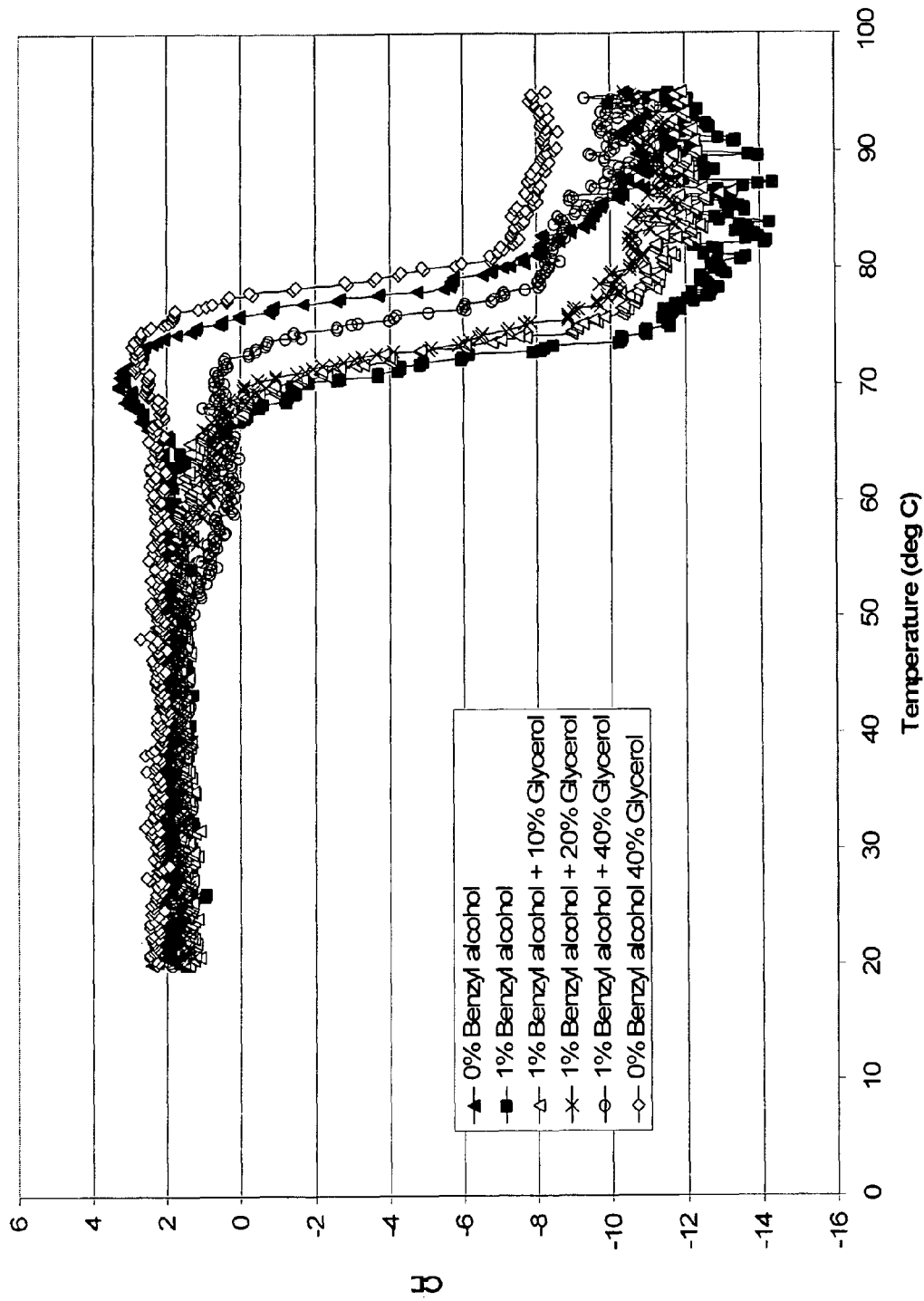
FIG. 10 is a representative graph displaying the effect of the destabilizing preservative benzyl alcohol on the stability of the antibody Rituxan®, in the absence of any osmolyte and in the presence of 10% and 40% glycerol, as measured using circular dichroism (CD).

Benzyl alcohol at 1% (0.097M) destabilizes Rituxan, lowering the melting temperature by more than 5° C. Adding increasing concentration of glycerol from 10% (1.357M) to 20% (2.714M) to 40% (5.428 M) stabilized Rituxan, increasing the meting temperature as measure by CD (see FIG. 10). TMAO destabilized Rituxan and caused the antibody to precipitate out of solution at 63° C. Glycine (1M) stabilized Rituxan but also caused a dip in the CD signal at around 35° C. The addition of 1M glycine and 10% (1.357M) glycerol showed an additive effect on the melting temperature of the antibody. The stabilization seen with 200 mM glycine was equivalent to that seen with 10% (1.357 M) glycerol.

Example 7

IgG1 Antibody 864G1

Figure 11:
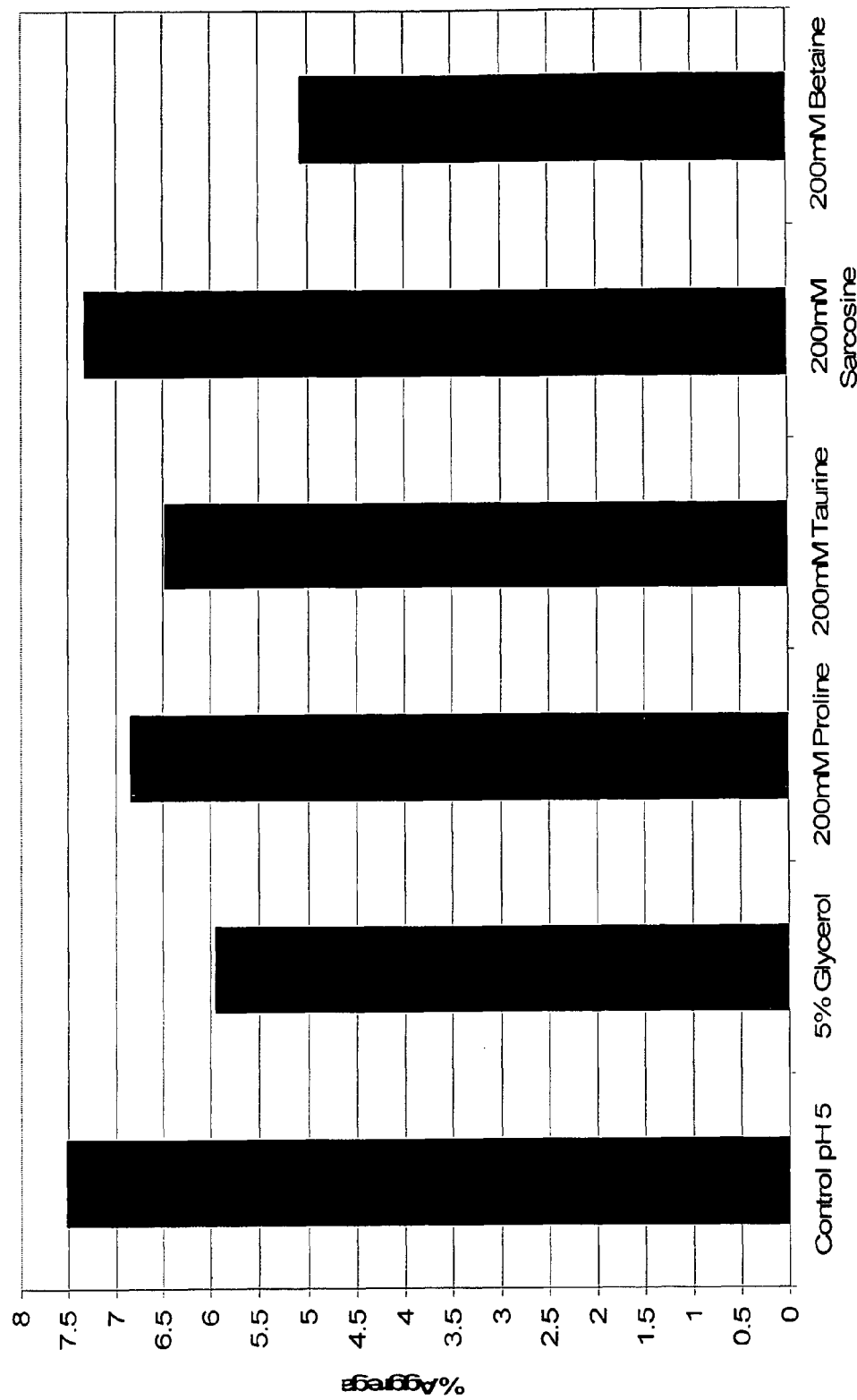
FIG. 11 is a graph showing aggregation of 864G1 (30 mg/mL), an IgG1 antibody, in a formulation having a destabilizing amount of benzyl alcohol in the absence of any osmolyte and in the presence of 5% (0.679 M) glycerol, 200 mM proline, 200 mM taurine, 200 mM sarcosine, and 200 mM betaine, as measured by size exclusion chromatography (SEC) and after 5 days at 52° C.

A. Formulations with Benzyl Alcohol and Various Osmolytes—Assessment of Aggregation A formulation of IgG1 antibody 864G1 was prepared to provide a 30 mg/mL concentration of the antibody and 20 mM sodium acetate at pH 5.00. A control formulation was set aside, having no osmolyte added, while five test formulations were prepared, each having a different osmolyte added. Glycerol (5% or 0.679 M), proline (0.200 M), taurine (0.200 M), sarcosine (0.200 M), and betaine (0.200 M) were analyzed for stabilizing ability. Each formulation was stored at 52° C. for 5 days. The amount of aggregation of 864G1 was measured using SEC. The results are shown in FIG. 11. All five osmolyte-containing formulations showed decreased aggregation in comparison to the formulation having no osmolyte. Betaine showed the most stabilizing ability.

Figure 12:
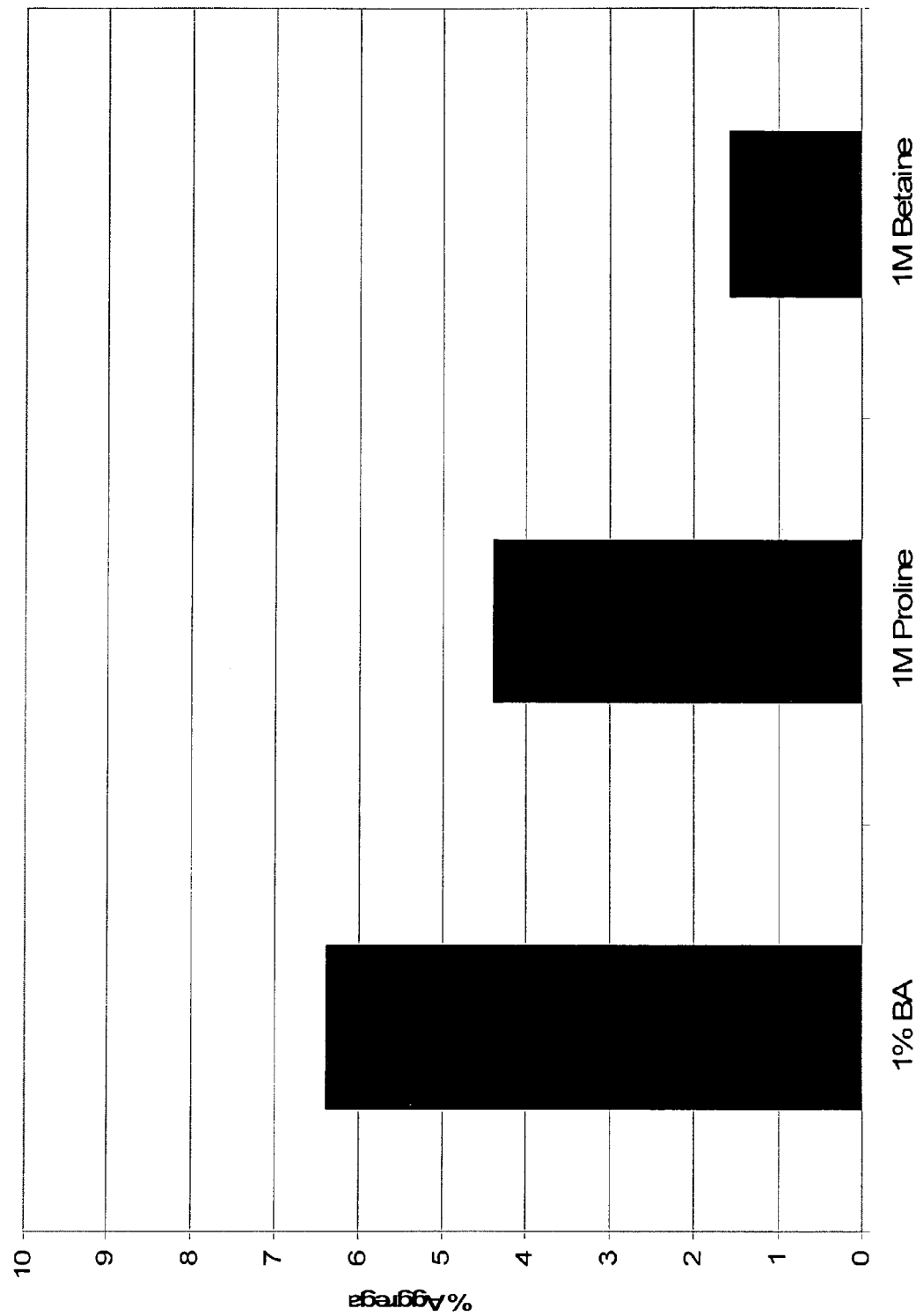
FIG. 12 is a graph showing aggregation of 864G1 (30 mg/mL) in formulations having a destabilizing amount of benzyl alcohol in the absence of any osmolyte and in the present of 1M proline or 1M betaine, as measured by SEC, after 4 days at 52° C.

B. Formulations with Benzyl Alcohol and Higher Concentrations Proline and Betaine—Assessment of Aggregation Formulations having higher concentrations of proline (1 M) and betaine (1 M) were prepared to provide a 30 mg/mL 864G1 concentration, 20 mM sodium acetate concentration, and at a pH 5.00. These formulations were stored at 52° C. for 4 days, then measured for amount aggregate formed. The results are provided in FIG. 12, showing that 1 M proline and betaine were successful in decreasing aggregation of 864G1, and that the higher concentrations of proline and betaine achieved a greater reduction in aggregation in comparison to the 0.200M formulations (above).

Figure 13:
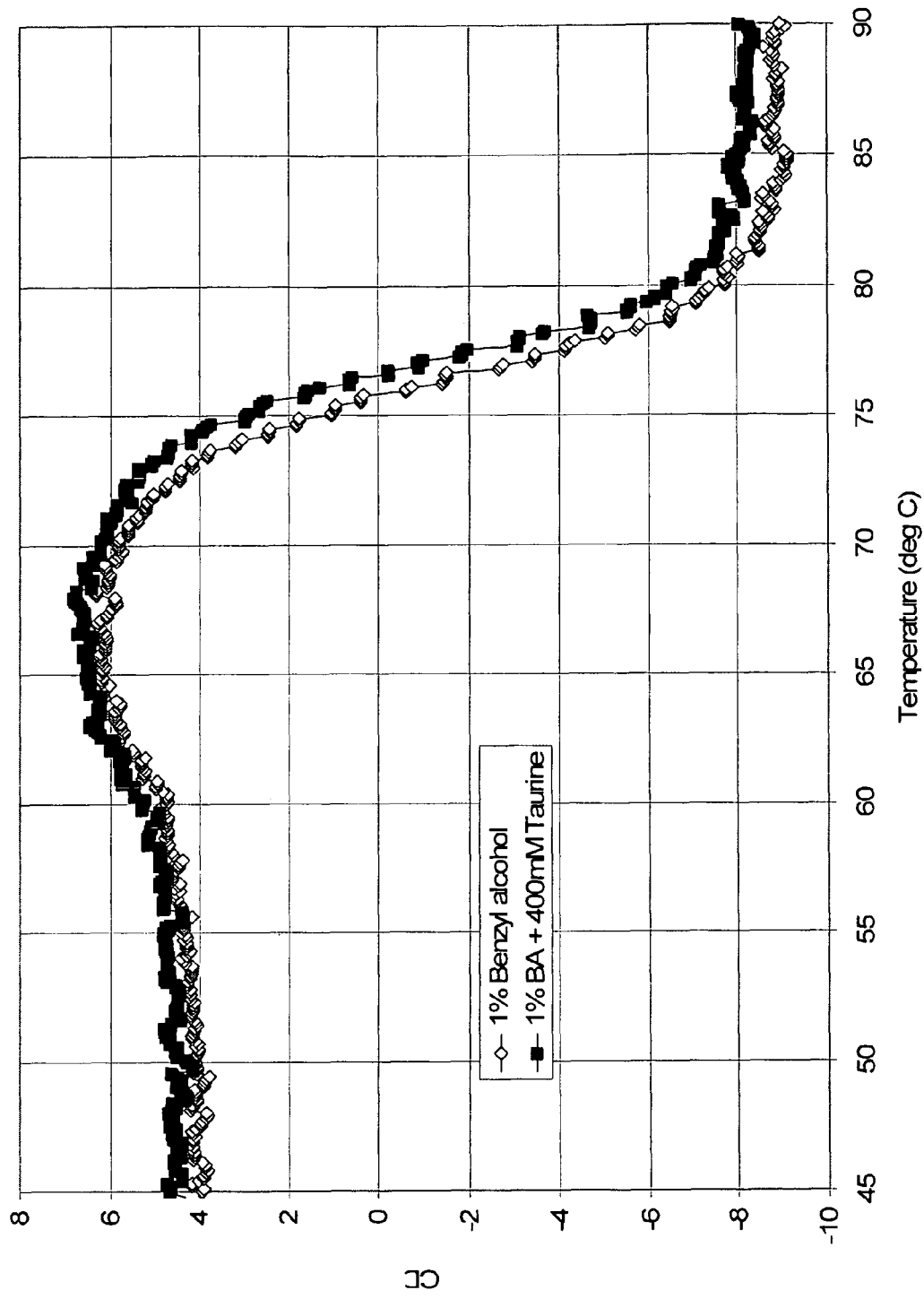
FIG. 13 is a graph displaying the effect of the destabilizing preservative benzyl alcohol on the stability of 864G1, in the absence of any osmolyte and in the presence of 0.40 M taurine, as measured using circular dichroism (CD).
Figure 14:
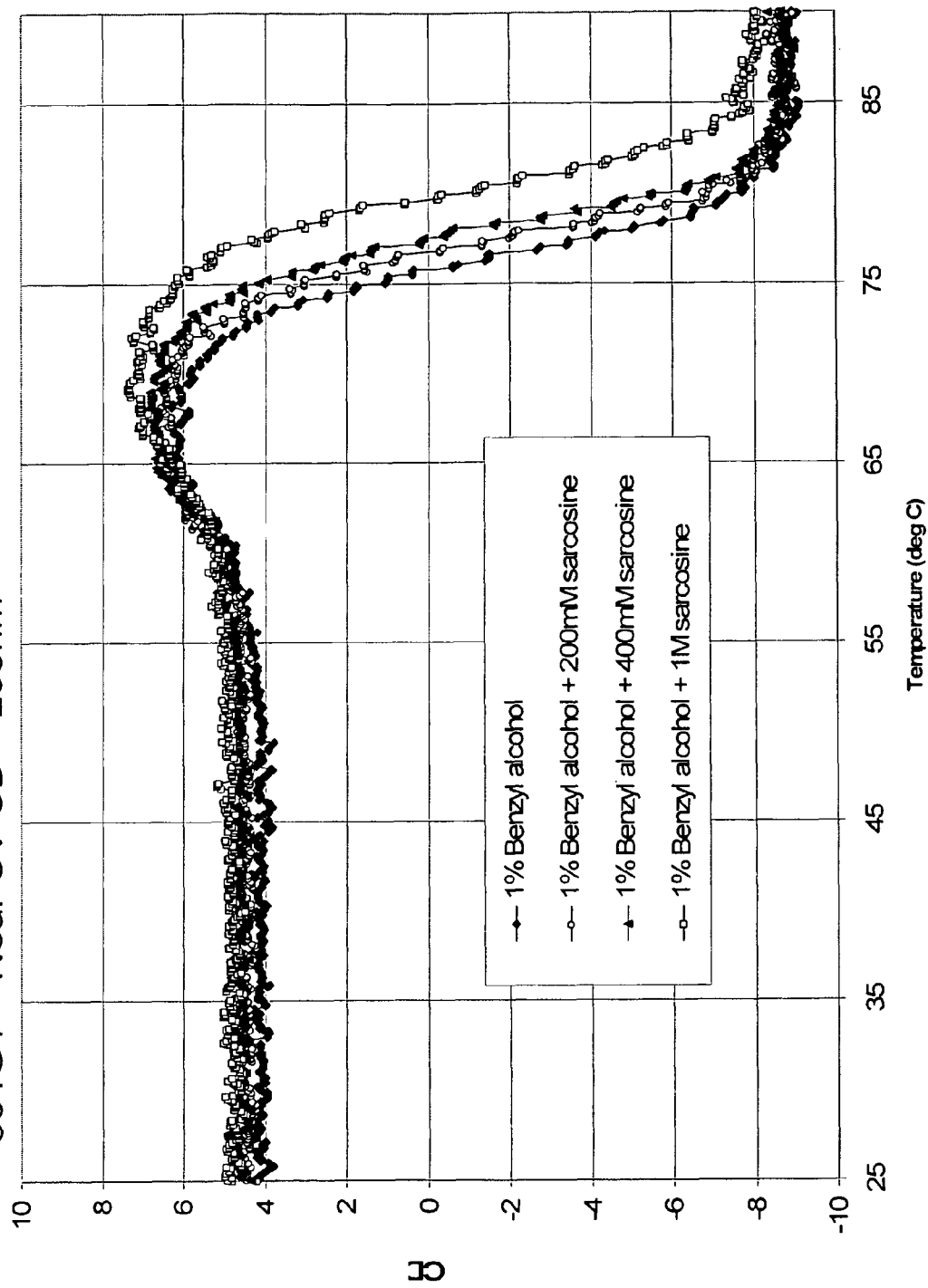
FIG. 14 is a graph displaying the effect of the destabilizing preservative benzyl alcohol on the stability of 864G1, in the absence of any osmolyte and in the presence of 0.20 M, 0.40 M, and 1.0 M sarcosine, as measured using circular dichroism (CD).
Figure 15:
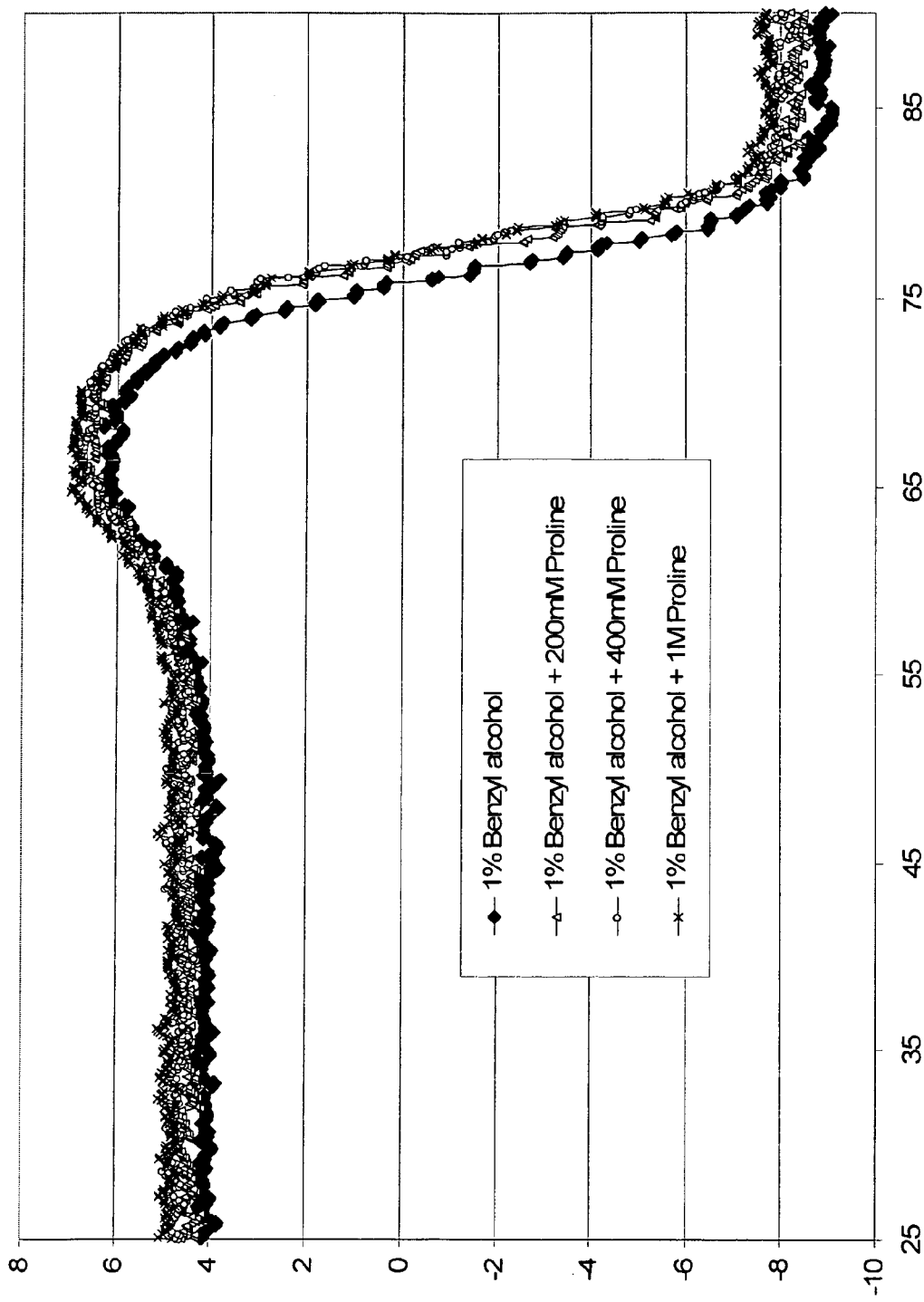
FIG. 15 is a graph displaying the effect of the destabilizing preservative benzyl alcohol on the stability of 864G1, in the absence of any osmolyte and in the presence of 0.20 M, 0.40 M, 1.0 M proline, as measured using circular dichroism (CD).
Figure 16:
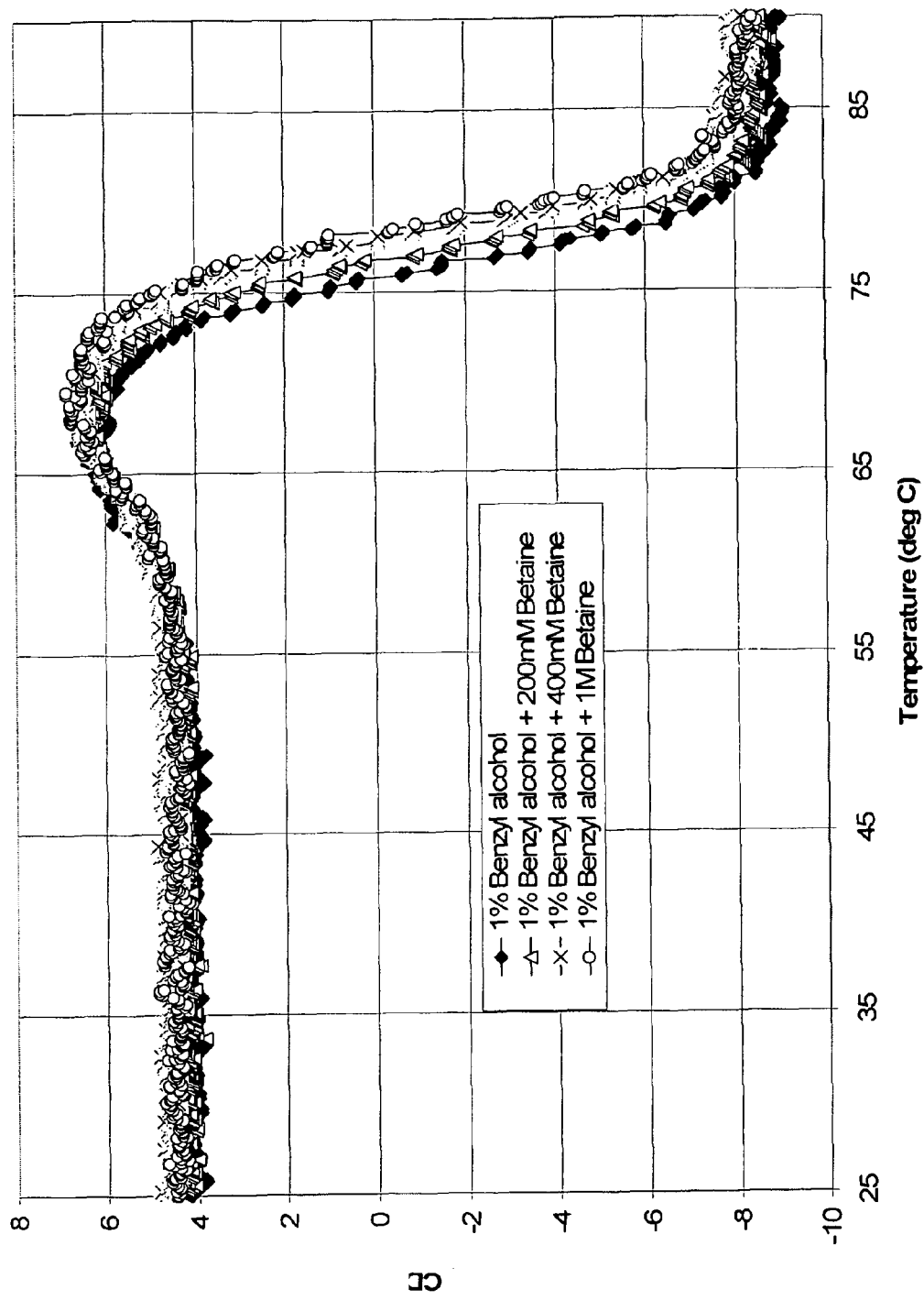
FIG. 16 is a graph displaying the effect of the destabilizing preservative benzyl alcohol on the stability of 864G1, in the absence of any osmolyte and in the presence of 0.40 M and 1.0 M betaine, as measured using circular dichroism (CD).

C. Formulations with Benzyl Alcohol and Osmolytes—Assessment of Thermal Stability Formulations of 864G1 (30 mg/mL), 20 mM sodium acetate, and benzyl alcohol (1% or 0.097M) at pH 5.00 were prepared both in the presence and absence of osmolytes. The formulations were assessed for stability by monitoring the CD spectra at 295 at a temperature range from 50 to 90° C. Taurine (0.40 M) stabilized the formulation (see FIG. 13), as did sarcosine (0.20 M, 0.40 M, and 1.0 M—FIG. 14), proline (0.20 M, 0.40 M, and 1.0 M—FIG. 15), and betaine (0.20 M, 0.40 M, and 1.0 M—FIG. 16).

Figure 17:
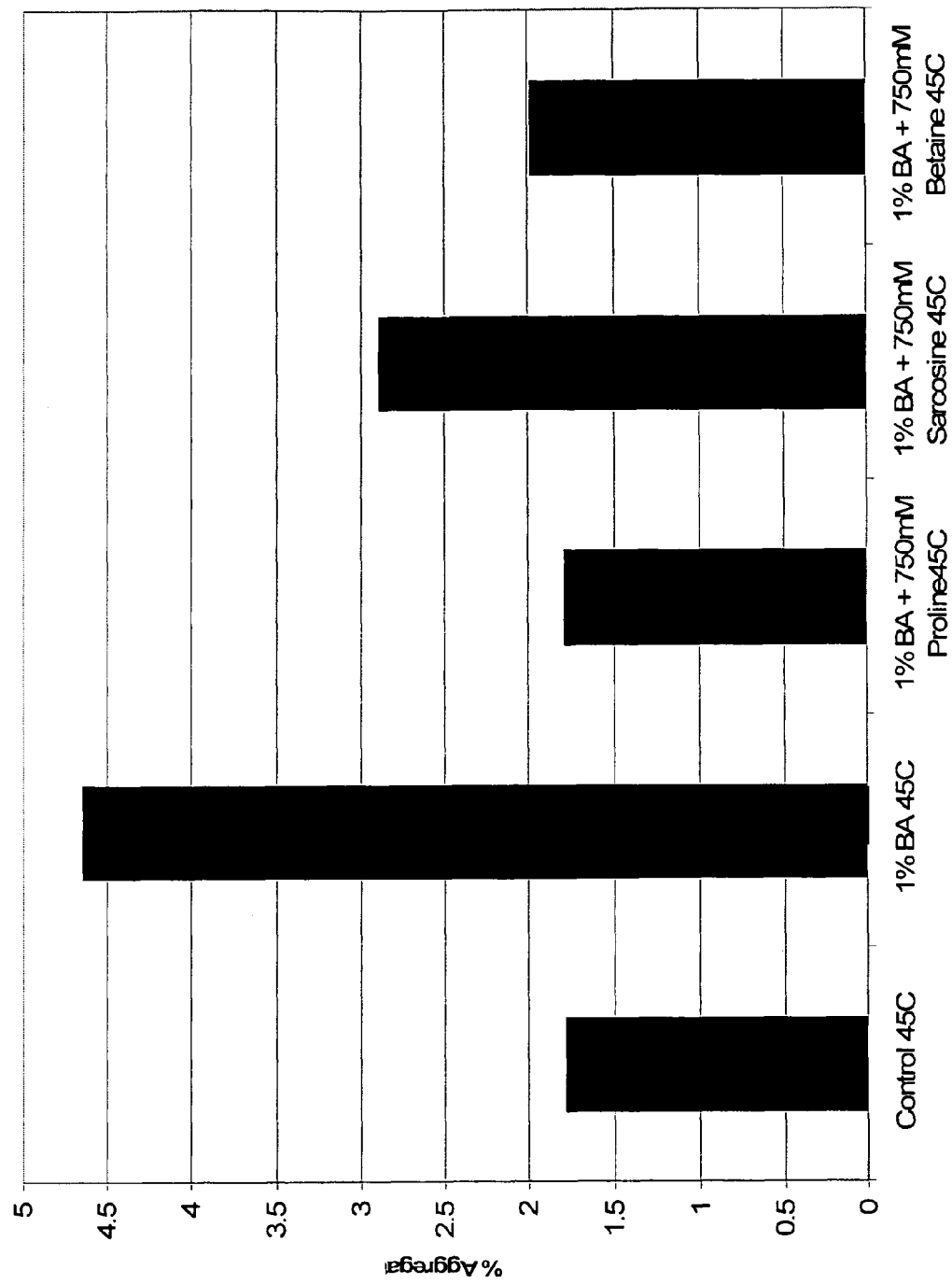
FIG. 17 is a graph showing aggregation of 864G1 (150 mg/mL) in a formulation, in the presence and absence of a destabilizing amount of benzyl alcohol (1% or 0.097 M), and in the presence or absence of an osmolyte: proline (0.750 M), sarcosine (0.750 M), and betaine (0.750 M), as measured by size exclusion chromatography (SEC) and after 4 days at 45° C.
Figure 18:
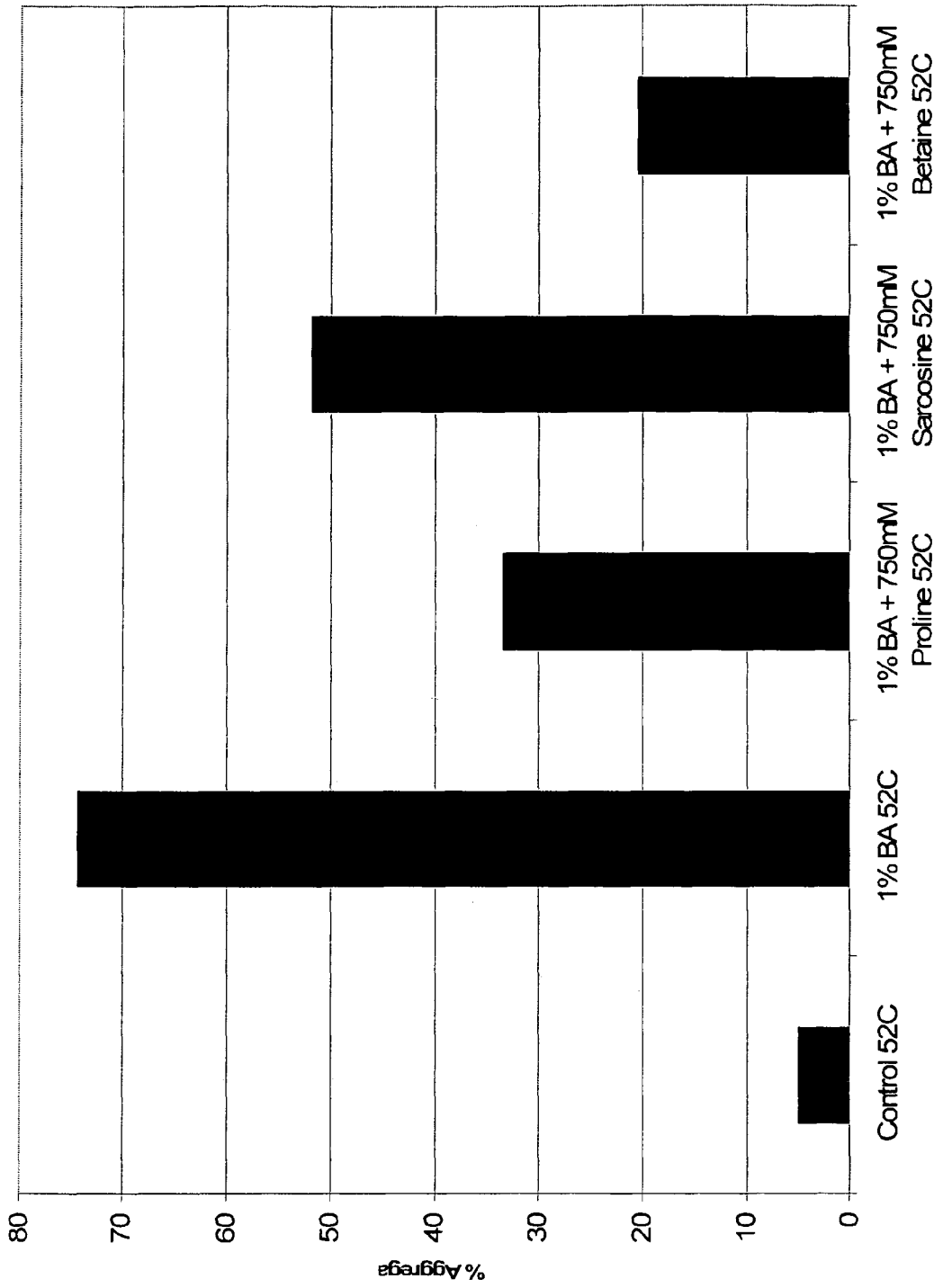
FIG. 18 is a graph showing aggregation of 864G1 (150 mg/mL) in a formulation, in the presence and absence of a destabilizing amount of benzyl alcohol (1% or 0.097 M), and in the presence or absence of an osmolyte: proline (0.750 M), sarcosine (0.750 M), and betaine (0.750 M), as measured by size exclusion chromatography (SEC) and after 4 days at 52° C.

D. Highly Concentrated Formulations with and without Benzyl Alcohol and Osmolytes—Assessment of Aggregation Formulations of 864G1 (150 mg/mL) and 20 mM sodium acetate at pH 5.00 were prepared in the presence and absence of a destabilizing amount of a preservative (benzyl alcohol 1% or 0.097 M) and osmolyte—0.750 M proline, sarcosine, or betaine. The stability of each formulation was analyzed after 4 days at either 45° C. (FIG. 17) or 52° C. (FIG. 18). This experiment showed that high concentrations of antibody can be stabilized with the addition of an osmolyte.

Example 8

Shelf Life Determination

The shelf-life of any of the above described formulations of the invention is measured by the stability of active protein in the pharmaceutical formulation that is stored under specified storage conditions, for example, 2-8° C.

The formulation to be tested is divided into four different batches. Each batch is stored at varying temperatures, for example, 4° C. (refrigerator), 25° C. (room temperature), 37° C., and 45° C., respectively. Shelf life of protein in the formulation is determined by the storage period during which the active protein undergoes minimal degradation when stored at 2-8° C. Degradation of protein in a pharmaceutical formulation can be detected using accelerated testing (also called stress testing) under exaggerated storage conditions designed to increase the rate of chemical or physical degradation of the drug substance. For example, a batch can be "stressed" (placed in chamber which maintains a temperature of 45 degrees centigrade and 75% humidity) for 90 days.

Samples of each batch of formulation are then analyzed at different time points (e.g., time zero, 2 weeks, 1 month, 3 months, 6 months, 9 months, and 1 year) for amount of therapeutic protein still present in the formulation compared to aggregates, fragments or unfolded or improperly folded protein. Samples stored under accelerated conditions such as higher temperatures (i.e., 25, 37 or 45° C.) are usually tested for degradation at time up to 3 months, while the stability under normal storage conditions (e.g., 2-8° C.) is monitored for up to 2 years to determine its shelf-life. For comparison, the same protein in two formulations either containing osmolyte and preservative or containing only preservative can be monitored to determine the beneficial effect of osmolyte on shelf-life.

Analysis of the therapeutic protein in the formulation may be carried out by a variety of detection methods: SEC-HPLC, RP-HPLC, ion exchange-HPLC, mass spectroscopy, fluorescence spectroscopy, CD spectroscopy, FT-IR, Raman spectroscopy, or a combination of any of these methods.

What is claimed is:

1. A stable aqueous sterile formulation comprising (a) Darbepoetin (SEQ. ID NO.: 1) or erythropoietin (SEQ. ID NO.: 2) or an erythropoietin analog with at least 90% homology to SEQ. ID NO.: 2 at a concentration of up to about 15 mg/ml, (b) a destabilizing concentration of benzyl alcohol at a concentration of at least about 0.065 M or benzalkonium chloride at a concentration of up to about 0.1 M, and (c) glycerol at a concentration of up to about 5 M or trimethylamine N-oxide at a concentration of up to about 2 M or proline at a concentration of up to about 2 M, wherein the concentration of glycerol, trimethylamine N-oxide or proline mitigates the destabilizing effect of said benzyl alcohol or benzalkonium chloride.

2. The stable aqueous sterile formulation of claim 1, wherein the Darbepoetin (SEQ. ID NO: 1) or erythropoietin (SEQ. ID NO.: 2) or an erythropoietin analog with at least 90% homology to SEQ. ID NO.: 2 is at a concentration ranging from about 0.5 to about 3 mg/mL, the benzalkonium chloride is at a concentration of up to about 0.1 M, and the glycerol is at a concentration of up to about 1.0 M.

3. The stable aqueous sterile formulation of claim 1, wherein the Darbepoetin (SEQ. ID NO: 1) or erythropoietin (SEQ. ID NO.: 2) or an erythropoietin analog with at least 90% homology to SEQ. ID NO.: 2 is at a concentration ranging from about 0.5 to about 3 mg/mL, the benzyl alcohol is at a concentration ranging from about 0.13 to about 0.15 M, and the glycerol is at a concentration of up to about 1.0 M.

4. The stable aqueous sterile formulation of claim 1, wherein the Darbepoetin (SEQ. ID NO: 1) or erythropoietin (SEQ. ID NO.: 2) or an erythropoietin analog with at least 90% homology to SEQ. ID NO.: 2 is at a concentration ranging from about 0.5 to about 3 mg/mL, the benzyl alcohol is at a concentration ranging from about 0.13 to about 0.15 M, and the trimethylamine N-oxide is at a concentration ranging from about 0.85 to about 1.15 M.

5. The stable aqueous sterile formulation of claim 1, wherein the Darbepoetin (SEQ. ID NO: 1) or erythropoietin (SEQ. ID NO.: 2) or an erythropoietin analog with at least 90% homology to SEQ. ID NO.: 2 is at a concentration ranging from about 0.5 to about 3 mg/mL, the benzyl alcohol is at a concentration ranging from about 0.13 to about 0.15 M, and the proline is at a concentration ranging from about 0.85 to about 1.15 M.

6. A stable aqueous sterile formulation comprising (a) Darbepoetin (SEQ. ID NO.: 1) or erythropoietin (SEQ. ID NO.: 2) or an erythropoietin analog with at least 90% homology to SEQ. ID NO.: 2 at a concentration of up to about 15 mg/ml, (b) a destabilizing concentration of benzyl alcohol at a concentration of at least about 0.065 M or benzalkonium chloride at a concentration of up to about 0.1 M, and (c) glycerol at a concentration of up to about 5 M or trimethylamine N-oxide at a concentration of between about 0.2 M to about 6.0 M or proline at a concentration of between about 0.2 M to about 6.0 M, wherein the concentration of glycerol, trimethylamine N-oxide or proline mitigates the destabilizing effect of said benzyl alcohol or benzalkonium chloride.

7. The stable aqueous sterile formulation of claim 1 or 6 produced by the method comprising the step of combining a therapeutic protein in an aqueous solution, a destabilizing concentration of a preservative, and an amount of osmolyte effective to mitigate the destabilizing effect of said preservative.

8. The stable aqueous sterile formulation of claim 1 or 6, wherein the concentration of benzyl alcohol is about 0.075 M to about 0.15 M.

9. The stable aqueous sterile formulation of claim 1 or 6, wherein, the concentration of glycerol is up to about 1.0 M.

10. The stable aqueous sterile formulation of claim 1 or 6, comprising up to about 1.0 M glycerol or about 0.85 M to about 1.15 M proline.

11. A method for preparing a lyophilized powder comprising the step of lyophilizing the aqueous formulation of claim 8.

12. A multidose formulation of the stable aqueous sterile formulation of claim 8 in a single vial.

13. A method for preparing a lyophilized powder comprising the step of lyophilizing the aqueous formulation of claim 9.

14. A multidose formulation of the stable aqueous sterile formulation of claim 9 in a single vial.

15. A method for preparing a lyophilized powder comprising the step of lyophilizing the aqueous formulation of claim 10.

16. A multidose formulation of the stable aqueous sterile formulation of claim 10 in a single vial.

17. The stable aqueous sterile formulation of claim 6, wherein the concentration of trimethylamine N-oxide or proline is between about 0.35 M to about 6.0 M.

18. The stable aqueous sterile formulation of claim 6, wherein the concentration of trimethylamine N-oxide or proline is between about 0.5 M to about 5.5 M.

19. The stable aqueous sterile formulation of claim 6, wherein the concentration of Darbepoetin or erythropoietin is about 0.1 mg/ml.

20. The stable aqueous sterile formulation of claim 6, wherein the concentration of Darbepoetin or erythropoietin is about 0.3 mg/ml.

21. The stable aqueous sterile formulation of claim 6, wherein the concentration of Darbepoetin or erythropoietin is about 0.5 mg/ml.

22. The stable aqueous sterile formulation of claim 6, wherein the concentration of Darbepoetin or erythropoietin is about 1.0 mg/ml.

23. The stable aqueous sterile formulation of claim 6, wherein the concentration of Darbepoetin or erythropoietin is between about 0.5 mg/ml to about 3 mg/ml.

24. A stable aqueous sterile formulation comprising (a) Darbepoetin (SEQ. ID NO.: 1) or erythropoietin (SEQ. ID NO.: 2) or an erythropoietin analog with at least 90% homology to SEQ. ID NO.: 2 at a concentration of between about 0.1 mg/ml to about 180 mg/ml, (b) a destabilizing concentration of benzyl alcohol at a concentration of at least about 0.065 M or benzalkonium chloride at a concentration of up to about 0.1 M, and (c) glycerol at a concentration of up to about 5 M or trimethylamine N-oxide at a concentration of between about 0.2 M to about 6.0 M or proline at a concentration of between about 0.2 M to about 6.0 M, wherein the concentration of glycerol, trimethylamine N-oxide or proline mitigates the destabilizing effect of said benzyl alcohol or benzalkonium chloride.

25. The stable aqueous sterile formulation of claim 24, wherein the concentration of Darbepoetin or erythropoietin is between about 0.3 mg/ml to about 150 mg/ml.

26. The stable aqueous sterile formulation of claim 24, wherein the concentration of Darbepoetin or erythropoietin is between about 0.5 mg/ml to about 3 mg/ml.

27. A method for preparing a lyophilized powder comprising the step of lyophilizing the aqueous formulation of any one of claim 2-5, 1, or 6-18, 19-26.

28. A method for reconstituting a lyophilized powder of claim 27, comprising the step of adding a sterile aqueous diluent.

29. A multidose formulation of any one of the stable aqueous sterile formulations of claim 2-5, 1 or 6-18, 19-26.

* * * * *

SEQUENCE LISTING

```
<160> NUMBER OF SEQ ID NOS: 2

<210> SEQ ID NO 1
<211> LENGTH: 193
<212> TYPE: PRT
<213> ORGANISM: Homo sapien
<220> FEATURE:
<221> NAME/KEY: mat_peptide
<222> LOCATION: (28)..(193)

<400> SEQUENCE: 1

Met Gly Val His Glu Cys Pro Ala Trp Leu Trp Leu Leu Leu Ser Leu
    -25                 -20                 -15
```

```
Leu Ser Leu Pro Leu Gly Leu Pro Val Leu Gly Ala Pro Pro Arg Leu
    -10              -5                  -1  1               5

Ile Cys Asp Ser Arg Val Leu Glu Arg Tyr Leu Leu Glu Ala Lys Glu
                10                  15                  20

Ala Glu Asn Ile Thr Thr Gly Cys Asn Glu Thr Cys Ser Leu Asn Glu
                25                  30                  35

Asn Ile Thr Val Pro Asp Thr Lys Val Asn Phe Tyr Ala Trp Lys Arg
                40                  45                  50

Met Glu Val Gly Gln Gln Ala Val Glu Val Trp Gln Gly Leu Ala Leu
    55                  60                  65

Leu Ser Glu Ala Val Leu Arg Gly Gln Ala Leu Leu Val Asn Ser Ser
70                  75                  80                  85

Gln Val Asn Glu Thr Leu Gln Leu His Val Asp Lys Ala Val Ser Gly
                90                  95                  100

Leu Arg Ser Leu Thr Thr Leu Leu Arg Ala Leu Gly Ala Gln Lys Glu
                105                 110                 115

Ala Ile Ser Pro Pro Asp Ala Ala Ser Ala Ala Pro Leu Arg Thr Ile
                120                 125                 130

Thr Ala Asp Thr Phe Arg Lys Leu Phe Arg Val Tyr Ser Asn Phe Leu
    135                 140                 145

Arg Gly Lys Leu Lys Leu Tyr Thr Gly Glu Ala Cys Arg Thr Gly Asp
150                 155                 160                 165

Arg

<210> SEQ ID NO 2
<211> LENGTH: 193
<212> TYPE: PRT
<213> ORGANISM: Homo sapien

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
                35                  40                  45

Ala Glu Asn Ile Thr Thr Gly Cys Ala Glu His Cys Ser Leu Asn Glu
                50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
                130                 135                 140

Ala Ile Ser Pro Pro Asp Ala Ala Ser Ala Ala Pro Leu Arg Thr Ile
145                 150                 155                 160
```

```
Thr Ala Asp Thr Phe Arg Lys Leu Phe Arg Val Tyr Ser Asn Phe Leu
            165                 170                 175

Arg Gly Lys Leu Lys Leu Tyr Thr Gly Glu Ala Cys Arg Thr Gly Asp
            180                 185                 190

Arg
```